US012586196B2

(12) United States Patent
    Liu

(10) Patent No.: US 12,586,196 B2
(45) Date of Patent: Mar. 24, 2026

(54) METHODS AND SYSTEMS FOR MEDICAL IMAGING

(71) Applicant: SHANGHAI UNITED IMAGING HEALTHCARE CO., LTD., Shanghai (CN)

(72) Inventor: Yilin Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 323 days.

(21) Appl. No.: 18/323,397

(22) Filed: May 24, 2023

(65) Prior Publication Data

US 2023/0386036 A1     Nov. 30, 2023

(30) Foreign Application Priority Data

May 24, 2022    (CN) .......................... 202210566784.9

(51) Int. Cl.
    *G06T 7/00*       (2017.01)
    *A61B 6/00*       (2006.01)
    *A61B 6/03*       (2006.01)
    *G06T 11/00*      (2006.01)

(52) U.S. Cl.
    CPC ............ *G06T 7/0014* (2013.01); *A61B 6/037* (2013.01); *A61B 6/5258* (2013.01); *G06T 11/005* (2013.01); *G06T 2207/10028* (2013.01); *G06T 2207/10104* (2013.01);
    (Continued)

(58) Field of Classification Search
    CPC . G06K 9/00; A61B 6/00; A61B 6/037; G16H 10/60; G06T 7/0014; G06T 11/005
    See application file for complete search history.

(56) References Cited

U.S. PATENT DOCUMENTS

| | | | |
|---|---|---|---|
| 7,142,636 B2 | 11/2006 | Hsieh et al. | |
| 8,767,908 B2 * | 7/2014 | Leahy et al. | ...................... 378/4 |
| 10,849,585 B1 * | 12/2020 | Teixeira et al. | .......... G06K 9/00 |

(Continued)

FOREIGN PATENT DOCUMENTS

| | | |
|---|---|---|
| CN | 104116519 B | 9/2016 |
| CN | 107123095 A | 9/2017 |

(Continued)

OTHER PUBLICATIONS

Lin, Yuxuan, Estimation of Missing CT Projection Data Based on Multiple Deep Networks, China Outstanding Master's Degree Thesis Database Medicine and Health Science and Technology Series, 2020, 67 pages.
Bai, Jianan, 2D/3D CT Reconstruction from Incomplete Projections by Using a Contextual Autoencoder Network, China Outstanding Master's Degree Thesis Database Medicine and Health Science and Technology Series, 2019, 68 pages.

(Continued)

*Primary Examiner* — Jayanti K Patel
(74) *Attorney, Agent, or Firm* — METIS IP LLC

(57) ABSTRACT

Methods and systems for medical imaging are provided. A method may include: obtaining radiation events; determining first response information based on the radiation events, the first response information including first time information of the radiation events; determining second response information based on the radiation events, the second response information including response information corresponding to an anomaly detection unit and lacking time information; and generating an image based on the first response information and the second response information.

20 Claims, 12 Drawing Sheets

(52) U.S. Cl.
CPC .............. *G06T 2207/20076* (2013.01); *G06T 2207/30096* (2013.01); *G06T 2210/41* (2013.01)

(56) References Cited

U.S. PATENT DOCUMENTS

| | | | |
|---|---|---|---|
| 11,961,164 B2 * | 4/2024 | Panin et al. ............ | G06T 11/00 |
| 2013/0304386 A1 | 11/2013 | Niu et al. | |
| 2017/0074995 A1 | 3/2017 | Laurence et al. | |
| 2019/0361136 A1 | 11/2019 | Song et al. | |
| 2021/0090694 A1 * | 3/2021 | Colley et al. ......... | G16H 10/60 |
| 2024/0335178 A1 * | 10/2024 | Kolthammer et al. .. | A61B 6/00 |

FOREIGN PATENT DOCUMENTS

| | | |
|---|---|---|
| CN | 111429545 A | 7/2020 |
| CN | 109498048 B | 8/2020 |
| CN | 111553960 A | 8/2020 |

OTHER PUBLICATIONS

Wang, Lei, CT Reconstruction from Incomplete Projections Based on Deep Generative Networks, China Outstanding Master's Degree Thesis Database Medicine and Health Science and Technology Series, 2019, 79 pages.
"[Depth Camera Series 2] Depth Camera Principle Revealed—Time of Flight (TOF)", Web page <https://blog.csdn.net/electech6/article/details/78349107>, Oct. 26, 2017.

* cited by examiner

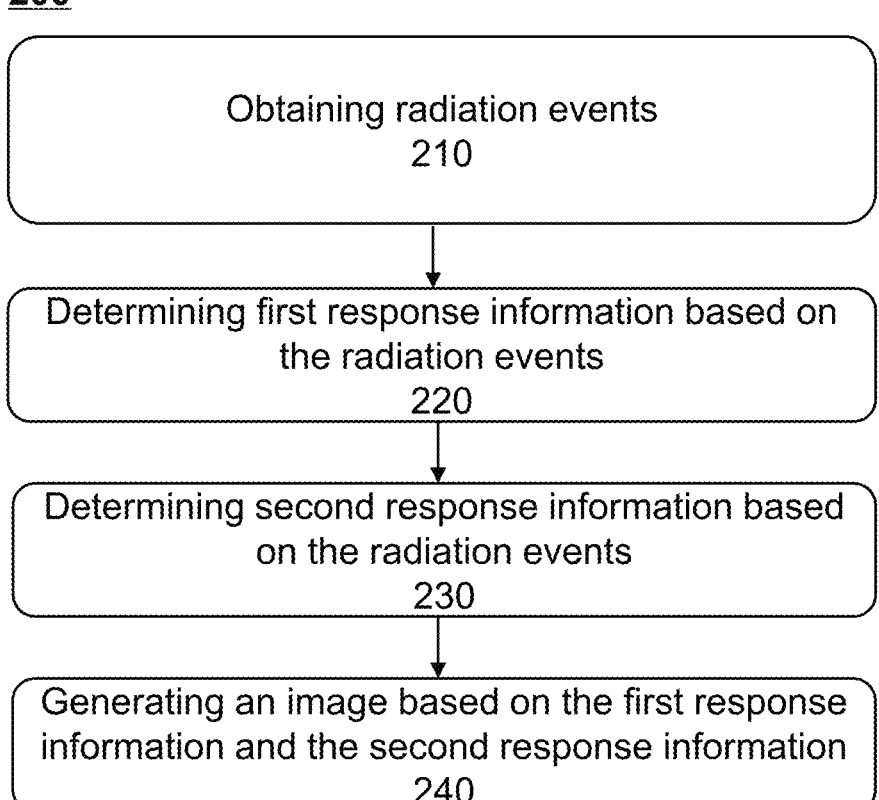
FIG. 2

<u>300</u>

```
┌─────────────────────────────────────────┐
│  Determining a time distribution of a    │
│  reference line of response based on the │
│  first time information of the first     │
│  response information                    │
│                  310                     │
└─────────────────────────────────────────┘
                     │
                     ▼
┌─────────────────────────────────────────┐
│  Determining a total count of radiation  │
│  events on the line of response          │
│  corresponding to the anomaly detection  │
│  unit                                    │
│                  320                     │
└─────────────────────────────────────────┘
                     │
                     ▼
┌─────────────────────────────────────────┐
│  Allocating the second time information  │
│  to the response information             │
│  corresponding to the anomaly detection  │
│  unit based on the time distribution and │
│  the total count of radiation events on  │
│  the line of response corresponding to   │
│  the anomaly detection unit              │
│                  330                     │
└─────────────────────────────────────────┘
```

Figure 4:
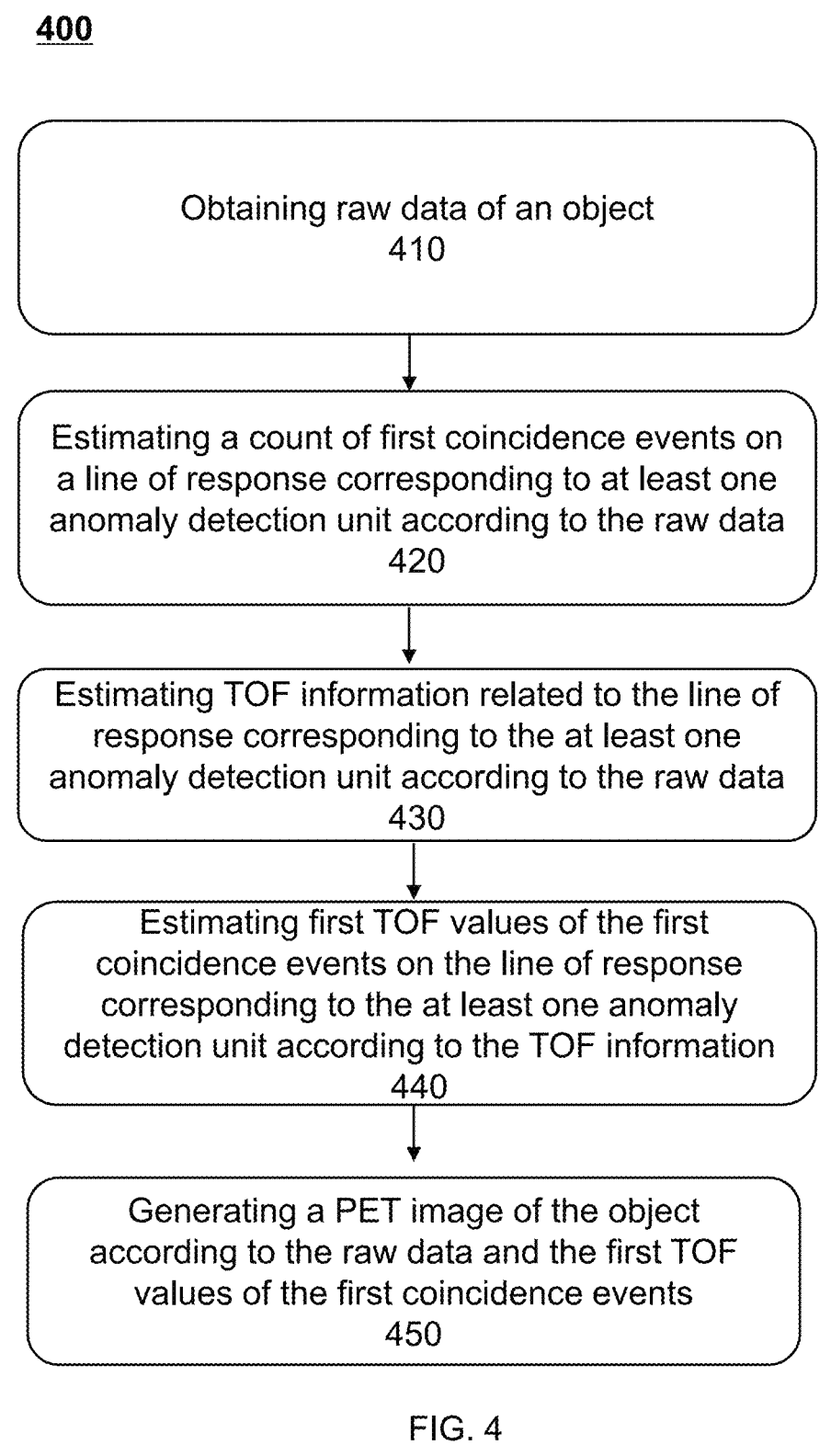

Obtaining raw data of an object
410

Estimating a count of first coincidence events on a line of response corresponding to at least one anomaly detection unit according to the raw data
420

Estimating TOF information related to the line of response corresponding to the at least one anomaly detection unit according to the raw data
430

Estimating first TOF values of the first coincidence events on the line of response corresponding to the at least one anomaly detection unit according to the TOF information
440

Generating a PET image of the object according to the raw data and the first TOF values of the first coincidence events
450

Generating a first sinogram according to raw
data
510

Generating a second sinogram based on the
first sinogram
520

Determining a count of first coincidence events
on a line of response corresponding to at least
one anomaly detection unit according to the
second sinogram
530

<u>600</u>

Generating an initial image of an object
according to raw data
610

Generating a third sinogram by performing a
forward projection on the initial image
620

Estimating TOF information related to a line of
response corresponding to at least one
anomaly detection unit according to the third
sinogram
630

<u>700</u>

Determining a count of second coincidence
events corresponding to each second TOF
value based on a third sinogram
710

↓

Determining a proportion of a count of second
coincidence events corresponding to the each
second TOF value to a total count of second
coincidence events as a probability value of
each second TOF value
720

↓

Determining TOF information related to a line
of response corresponding to at least one
anomaly detection unit according to the
probability value of each second TOF value
730

↓

For each first coincidence event, allocating a
second TOF value to the first coincidence
event as a first TOF value of the first
coincidence event according to the TOF
information
740

FIG. 7

Normal sinogram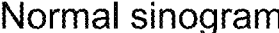
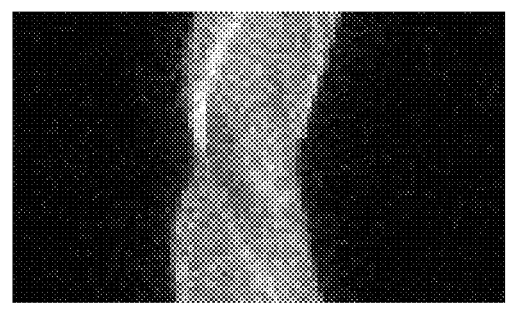
910
Bad channel sinogram
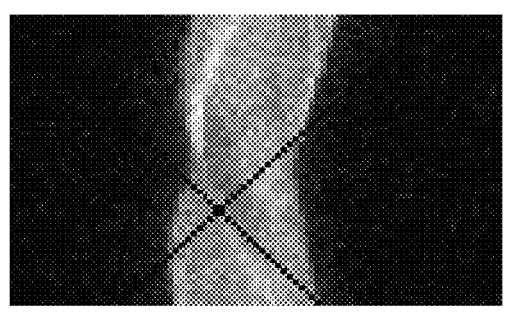
920
FIG. 9

Figure 11:
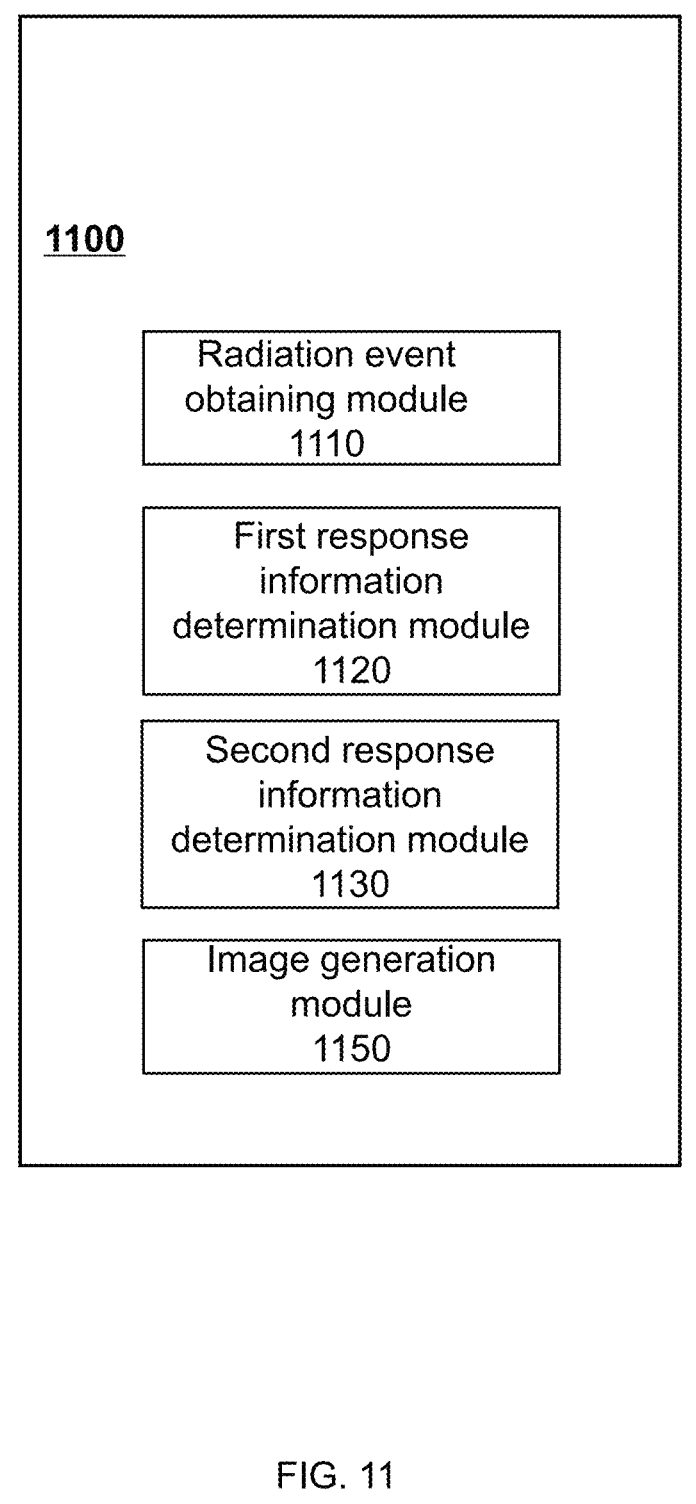

1100

Radiation event
obtaining module
1110

First response
information
determination module
1120

Second response
information
determination module
1130

Image generation
module
1150

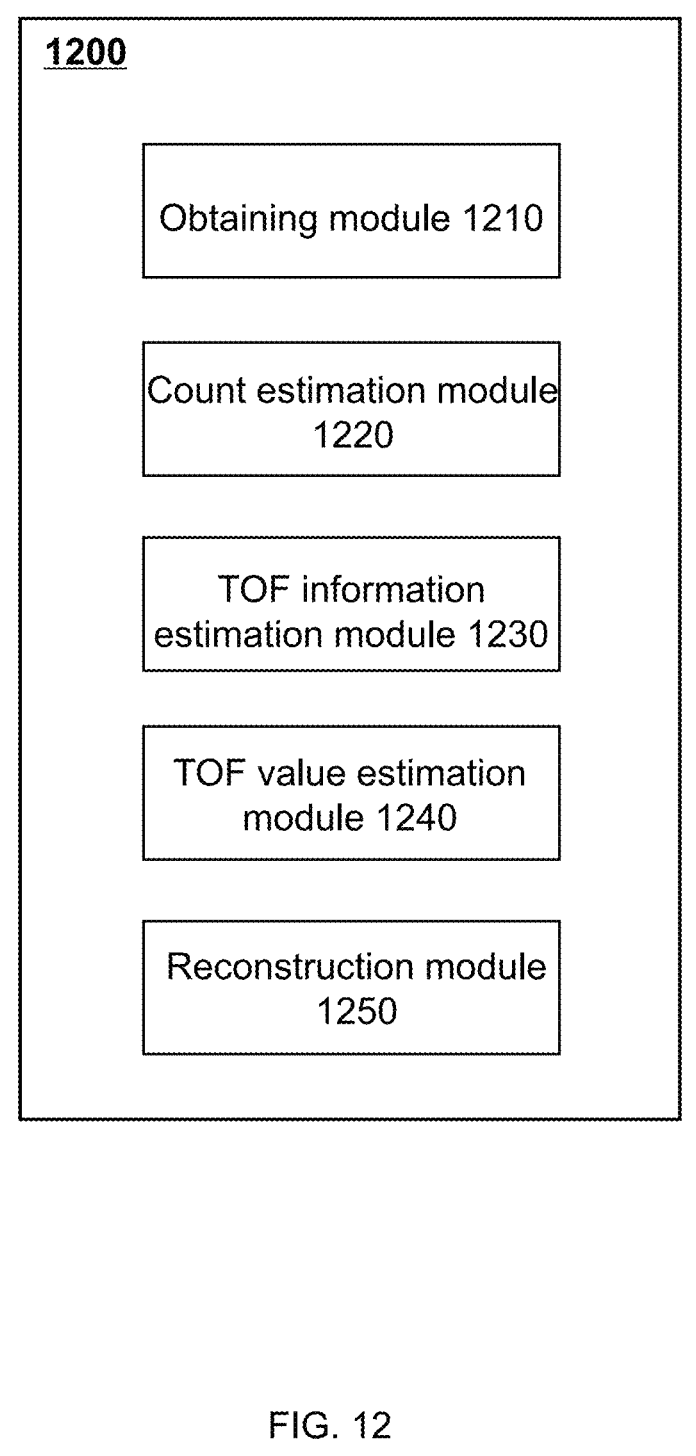

Obtaining module 1210

Count estimation module 1220

TOF information estimation module 1230

TOF value estimation module 1240

Reconstruction module 1250

FIG. 12

METHODS AND SYSTEMS FOR MEDICAL IMAGING

CROSS-REFERENCE TO RELATED APPLICATIONS

This application claims priority to Chinese Patent Application No. 202210566784.9, filed on May 24, 2022, the entire contents of which are hereby incorporated herein by reference.

TECHNICAL FIELD

The present disclosure relates to the field of medical imaging, and in particular, to methods and systems for medical imaging.

BACKGROUND

A medical image refers to an image of internal tissues and organs of the object obtained by interacting with a human body or an experimental object in a non-invasive way with the help of a medium. The medical image may assist a doctor in the diagnosis and treatment of diseases, and the quality of the medical image has an important impact on assisting the doctor in diagnosing patients' conditions.

Therefore, it is desirable to provide methods and systems for medical imaging to obtain a high-quality medical image.

SUMMARY

One or more embodiments of the present disclosure provide a method for medical imaging. The method may include: obtaining radiation events; determining first response information based on the radiation events, the first response information including first time information of the radiation events; determining second response information based on the radiation events, the second response information including response information corresponding to an anomaly detection unit and lacking time information; and generating an image based on the first response information and the second response information.

In some embodiments, the generating the image based on the first response information and the second response information may include: for the response information corresponding to the anomaly detection unit, obtaining updated second response information by allocating second time information to the response information based on the first time information; and generating the image based on the updated second response information.

In some embodiments, for the response information corresponding to the anomaly detection unit, the obtaining the updated second response information by allocating the second time information to the response information based on the first time information may include: determining a time distribution of a reference line of response based on the first time information of the first response information, wherein the reference line of response has a position correspondence relationship with a line of response corresponding to the anomaly detection unit; determining a total count of radiation events on the line of response corresponding to the anomaly detection unit; and allocating the second time information to the second response information based on the time distribution and the total count of radiation events on the line of response corresponding to the anomaly detection unit.

In some embodiments, the time distribution may include a distribution of Time of Flight differences in different periods of time.

In some embodiments, the allocating the second time information to the second response information based on the time distribution and the total count of radiation events on the line of response corresponding to the anomaly detection unit may include: for each radiation event on the line of response corresponding to the anomaly detection unit, determining a Time of Flight based on a period of time of the different periods of time.

In some embodiments, the method may further include: converting the time distribution into a probability distribution, wherein the probability distribution is configured to reflect a probability of allocating a certain period of time to each radiation event on the line of response corresponding to the anomaly detection unit.

In some embodiments, an accuracy level of the first response information and an accuracy level of the second response information may be adjustable.

In some embodiments, the determining the first response information based on the radiation events may include: generating a second image based on the radiation events; and determining the first response information based on the second image.

In some embodiments, the radiation events may include first radiation events. Each of the first radiation events may have a corresponding Time of Flight. The generating the second image based on the radiation events may include: for each first radiation event of the first radiation events, determining an ideal annihilation position according to a Time of Flight corresponding to the first radiation event; obtaining a broadened annihilation position by broadening the ideal annihilation position; and generating the second image based on the broadened annihilated positions.

In some embodiments, the determining the first response information based on the second image may include: obtaining a forward projection result by performing a forward projection on the second image; and determining the first response information based on the forward projection result.

In some embodiments, the determining the second response information based on the radiation events may include: obtaining initial response information based on the radiation events; and determining the second response information by performing a data repair process on the initial response information.

One or more embodiments of the present disclosure provide a system for medical imaging. The system may include: at least one storage device storing a set of instructions; and at least one processor in communicate with the storage device, wherein when executing the set of instructions, the at least one processor is configured to cause the system to perform operations including: obtaining radiation events; determining first response information based on the radiation events, the first response information including first time information of the radiation events; determining second response information based on the radiation events, the second response information including response information corresponding to an anomaly detection unit and lacking time information; and generating an image based on the first response information and the second response information.

In some embodiments, the at least one processor may be further configured to cause the system to perform operations including: for the response information corresponding to the anomaly detection unit, obtaining updated second response information by allocating second time information to the response information based on the first time information; and reconstructing the image based on the updated second response information.

In some embodiments, the at least one processor may be further configured to cause the system to perform operations including: determining a time distribution of a reference line of response based on the first time information of the first response information, wherein the reference line of response has a position correspondence relationship with a line of response corresponding to the anomaly detection unit; determining a total count of radiation events on the line of response corresponding to the anomaly detection unit; and allocating the second time information to the second response information based on the time distribution and the total count of radiation events on the line of response corresponding to the anomaly detection unit.

In some embodiments, the time distribution may include a distribution of Time of Flight differences in different periods of time.

In some embodiments, the at least one processor may be further configured to cause the system to perform operations including: for each radiation event on the line of response corresponding to the anomaly detection unit, determining a Time of Flight based on a period of time of the different periods of time.

In some embodiments, the at least one processor may be further configured to cause the system to perform operations including: converting the time distribution into a probability distribution, wherein the probability distribution is configured to reflect a probability of allocating a certain period of time to each radiation event on the line of response corresponding to the anomaly detection unit.

In some embodiments, an accuracy level of the first response information and an accuracy level of the second response information may be adjustable.

In some embodiments, the at least one processor may be further configured to cause the system to perform operations including: generating a second image based on the radiation events; and determining the first response information based on the second image.

In some embodiments, the radiation events may include first radiation events. Each of the first radiation events may have a corresponding Time of Flight. The at least one processor may be further configured to cause the system to perform operations including: for each first radiation event of the first radiation events, determining an ideal annihilation position according to a Time of Flight corresponding to the first radiation event; obtaining a broadened annihilation position by broadening the ideal annihilation position; and generating the second image based on the broadened annihilated positions.

In some embodiments, the at least one processor may be further configured to cause the system to perform operations including: obtaining a forward projection result by performing a forward projection on the second image; and determining the first response information based on the forward projection result.

In some embodiments, the at least one processor may be further configured to cause the system to perform operations including: obtaining initial response information based on the radiation events; and determining the second response information by performing a data repair process on the initial response information.

One or more embodiments of the present disclosure provide a method for positron emission tomography (PET). The method for PET may include obtaining raw data of an object, the raw data being obtained by detecting gamma photons by a plurality of detection units of a PET detector and the plurality of detection units including at least one anomaly detection unit; determining a count of first coincidence events on a line of response corresponding to the at least one anomaly detection unit according to the raw data; determining Time of Flight information related to the line of response corresponding to the at least one anomaly detection unit according to the raw data; determining a first Time of Flight value of each of the first coincidence events on the line of response corresponding to the at least one anomaly detection unit according to the Time of Flight information; and generating a PET image of the object according to the raw data and the first Time of Flight value of the each first coincidence event.

In some embodiments, the determining the count of the first coincidence events on the line of response corresponding to the at least one anomaly detection unit according to the raw data may include: generating a first sinogram according to the raw data, the count of first coincidence events on the line of response corresponding to the at least one anomaly detection unit in the first sinogram being abnormal; and generating a second sinogram according to the first sinogram, the second sinogram including the count of the first coincidence events on the line of response corresponding to the at least one anomaly detection unit.

In some embodiments, the determining Time of Flight information related to the line of response corresponding to the at least one anomaly detection unit according to the raw data may include: generating an initial image of the object according to the raw data; generating a third sinogram by performing a forward projection on the initial image; and determining the TOF information related to the line of response corresponding to the at least one anomaly detection unit according to the third sinogram.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which the same reference numbers represent the same structures, wherein:

FIG. 2 is a flowchart illustrating an exemplary process for medical imaging according to some embodiments of the present disclosure;

FIG. 3 is a flowchart illustrating an exemplary process for allocating second time information to response information corresponding to an anomaly detection unit according to some embodiments of the present disclosure;

FIG. 4 is a flowchart illustrating an exemplary process for positron emission tomography (PET) according to some embodiments of the present disclosure;

5

6

Figure 8:
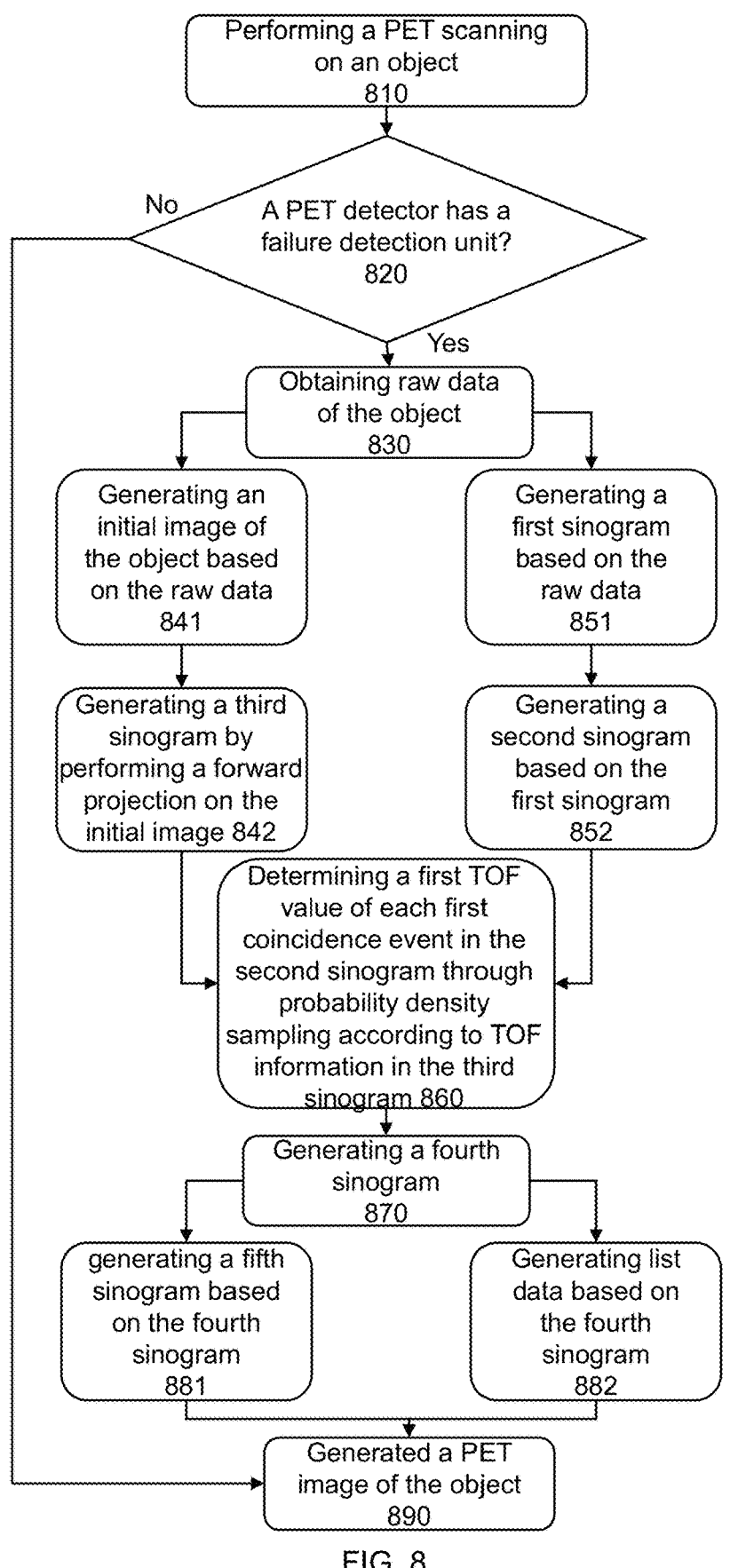
Figure 10:
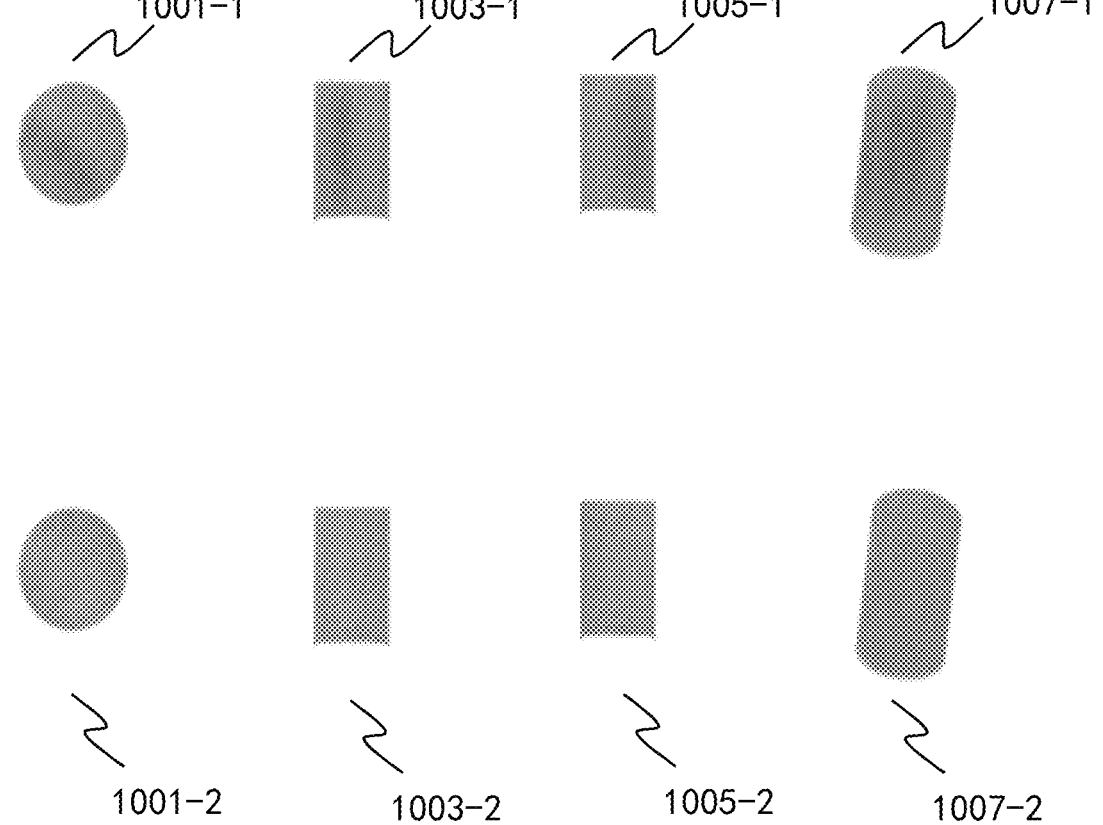

FIG. 7 is a flowchart illustrating an exemplary process for recovering TOF values of coincidence events on a line of response corresponding to a bad channel (i.e., at least one anomaly detection unit) according to some embodiments of the present disclosure;

FIG. 8 is a flowchart illustrating an exemplary process for PET imaging according to some embodiments of the present disclosure;

FIG. 9 are an exemplary bad channel sinogram and an exemplary normal sinogram according to some embodiments of the present disclosure;

FIG. 10 are exemplary initial sinograms and repaired sinograms according to some embodiments of the present disclosure;

FIG. 11 is a block diagram illustrating an exemplary medical imaging system according to some embodiments of the present disclosure; and FIG. 12 is a block diagram illustrating an exemplary imaging system according to some embodiments of the present disclosure.

DETAILED DESCRIPTION

In order to more clearly illustrate the technical solutions related to the embodiments of the present disclosure, a brief introduction of the drawings referred to the description of the embodiments is provided below. Obviously, drawings described below are only some examples or embodiments of the present disclosure. Those skilled in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that the system implements according to the embodiment of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

Figure 1:
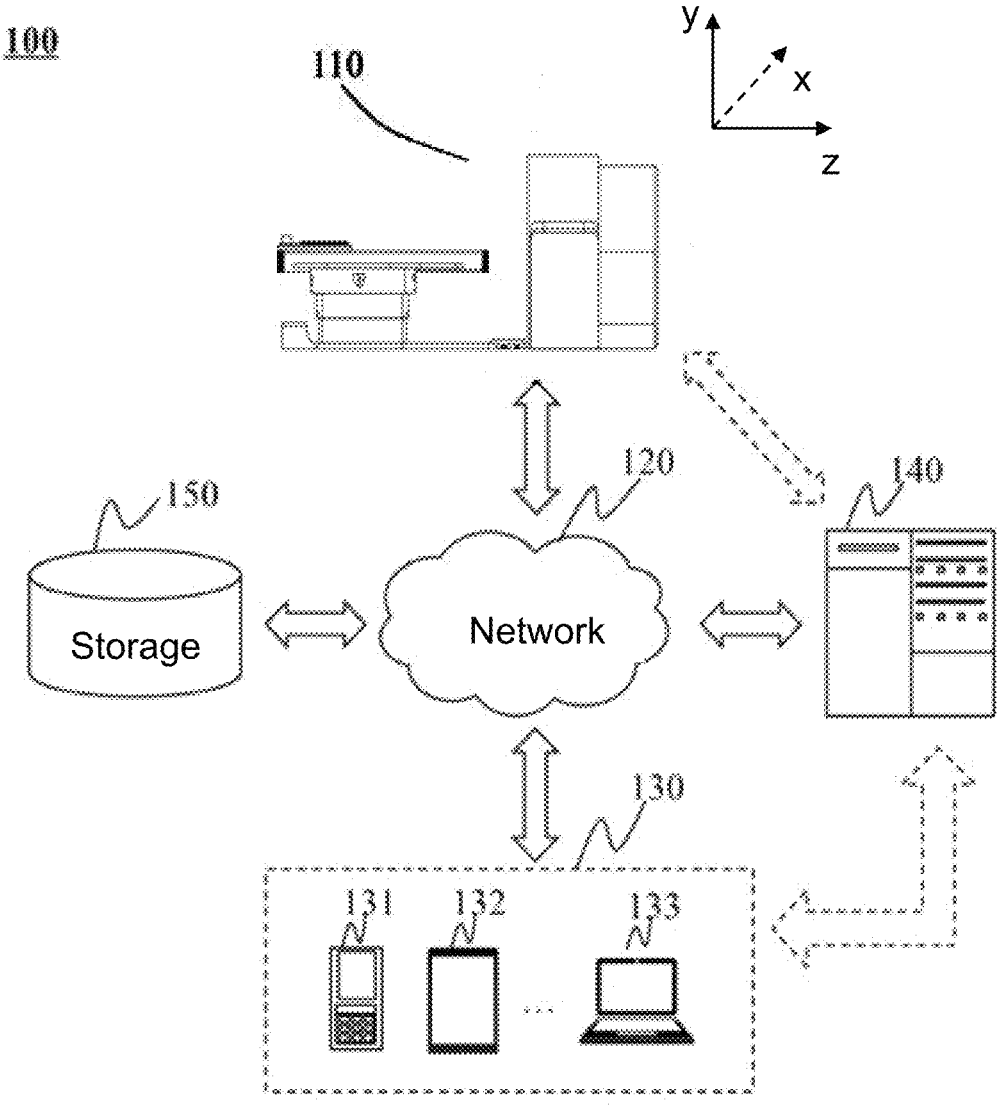
FIG. 1 is a schematic diagram illustrating an exemplary medical imaging system according to some embodiments of the present disclosure.

A positron emission tomography (PET) device, as a nuclear medicine imaging equipment, may be widely used in diagnosis, treatment, and/or research of a disease (e.g., a tumor). In recent years, a continuous increase of an axial field of view may be a main development trend of the PET device. The axial field of view of the PET device refers to a range covered by an image captured by the PET device in an axial direction (e.g., a long axis direction of a scanning bed or a Z-axis direction as shown in FIG. 1). On the one hand, a long axial field of view may bring a huge improvement in detection sensitivity, and further reduce a radiation dose to an object and improve a signal-to-noise ratio of a reconstructed image. On the other hand, however, a longer axial field of view corresponds to more PET detector modules (e.g., detection units), which may greatly increase a probability of a failure/anomaly module (also referred to as "a bad channel") in the system. The bad channel may cause collected PET raw data to include abnormal data (e.g., an abnormal count of coincidence events). If the raw data including the abnormal count is directly used for traditional PET image reconstruction, an image artifact and/or quantitative abnormality may exist, which may seriously affect clinic diagnosis.

In related technologies, when a damaged detector module of the imaging device (e.g., PET device) causes the raw data including the abnormal data corresponding to the bad channel (e.g., the abnormal count of coincidence events on a line of response corresponding to the bad channel), the PET image reconstruction may be performed using the following manners.

First, the image reconstruction may be performed by a reconstruction system modeling. In the system modeling, influence of the Line of Response (LOR) related to the bad channel may be removed (i.e., assuming that the system does not have a detector module corresponding to the bad channel), which may be achieved through an iteration equation of OP-OSEM as follows:

$$f_j^{(n+1)} = \frac{f_j^{(n)}}{\sum_i A_i \cdot N_i \cdot a_{ij}} \sum_i a_{ij} \frac{g_i}{\sum_{j'} a_{ij'} f_{j'}^{(n)} + \frac{R_i + S_i}{A_i \cdot N_i}},$$

where $a_{ij}$ denotes a system response matrix, i denotes a serial number of a line of response, and j denotes a serial number of a reconstructed image pixel. In principle, all $a_{ij}$ of $i \in I_{bad}$ (i.e., the line of response corresponding to the bad channel) should be set to 0. Since the natural count value $g_i$ of the bad channels is 0, no special processing may be required for $a_{ij}$ of the second half of the equation, as long as $\sum_i A_i N_i a_{ij}$ (i.e., sensitivity matrix) of the first half is modified. The specific way may include before calculating sensitivity matrix back-projection, setting the count of corresponding LORs to 0 and then perform a back-projection.

Second, the image reconstruction may be performed by sinogram repair, which may estimate data collected by the bad channel rather than changing the reconstruction system modeling. The estimated data may be added to a reconstruction data set for traditional reconstruction. For example, the sinogram repair may be performed through interpolations. As another example, the sinogram repair may be performed through a deep learning (e.g., artificial intelligence (AI)) process.

According to research and analysis, it may be found that in the above two manners, removing the line of response related to the bad channel in the reconstruction system modeling may alleviate a problem of image artifacts to a certain extent, but may not repair a quantitative deviation (e.g., quantification deviation of a tracer metabolic process in vivo). Although sinogram repair can remove image artifacts and recover image quantification to some extent, an interpolation or convolutional neural networks may often be required, so it is necessary to have a sufficient amount of statistics on the sinogram. The statistical means that information of enough data points around a certain data point is known, so as to ensure the accuracy of the sinogram repair performed through interpolation. However, an amount of data collected by normal clinical practice may merely guarantee the statistics on the non-Time of Flight (non-TOF) sinogram. If the sinogram is rearranged into a Time of Flight (TOF) sinogram, a count of sinograms in each TOF dimension may decrease more than an order of magnitude, resulting in the impossibility of the interpolation or deep learning repair. Therefore, sinogram repair may usually only be performed on the non-TOF sinogram, and the Time of Flight information (i.e., TOF information) of the repair event may not be obtained.

In view of this, some embodiments of the present disclosure provide methods and systems for medical imaging, which may obtain a high-quality medical image and assist a doctor in diagnosing patients' conditions.

FIG. 1 is a schematic diagram illustrating an exemplary medical imaging system according to some embodiments of the present disclosure.

As shown in FIG. 1, the imaging system 100 may include an imaging device 110, a network 120, one or more terminals 130, a processing device 140, and a storage 150.

The imaging device 110 may be configured to scan an object to collect scan data related to the object. The scan data may be configured to generate one or more images of the object. In some embodiments, the imaging device 110 may include a positron emission tomography (PET) device, a single photon emission computed tomography (SPECT) device, etc. In some embodiments, the imaging device 110 may further include a computed tomography (CT) device, a magnetic resonance imaging (MRI) device, etc. For example, the imaging device may include a multimodal PET-CT device, a PET-MRI device, a SPECT-CT device, a SPECT-MRI device, etc. The imaging device 110 may be configured to scan the object (e.g., a patient) or a portion thereof to generate an image of the object or a portion thereof. The image may include a PET image, a PET-MR image, a PET-CT image, etc. Merely for the purpose of illustration, the imaging device 110 is described below as an example of the PET device (also referred to as the imaging device 110).

The imaging device 110 may include a gantry, a detector, a detection region, a scanning bed, etc. A PET tracer may be given to the object before a scanning process begins. During a PET scanning, the PET tracer may emit a positron, i.e., an antiparticle of an electron. The positron has the same mass and opposite charge as the electron. An annihilation (also referred to as an "annihilation event" or "coincidence event" or "radiation event") may occur when the positron and the electron (which is naturally present in the object) interact. An electron-positron annihilation event may produce two 511 keV γ photons (i.e., a pair of γ photons), which travel in opposite directions relative to each other. A line connecting a pair of γ photons may be referred to as a "Line of Response (LOR)". In some embodiments, the PET tracer may include an element such as carbon (11C), nitrogen (13N), oxygen (15O), fluorine (18F), or the like, or any combination thereof. For example, the PET tracer may be an organic compound that contain one or more of the element labels. In the present disclosure, the annihilation event, the coincidence event, and radiation event may be used interchangeably.

Taking the PET tracer as fluoroglucose (e.g., fluorine-labeled glucose) as an example, a degree of glucose aggregation in the object may be obtained through a PET scanning. The more glucose aggregates in a region, the more vigorous the metabolism in the region, and the higher the probability that a lesion (e.g., a tumor, etc.) may be located in the region. During the PET scanning process, after the object absorbs the fluoroglucose, the annihilation (i.e., the annihilation event, the coincidence event, or the radiation event) may occur at an absorbed spatial position, and the pair of γ photons may be emitted in the opposite directions of each end and travel at the speed of light. The detector may include a plurality of detector modules arranged in one or more detector rings. An annihilation event may be detected by two detector modules arranged opposite to each other. The LOR of the annihilation event may pass through the two detector modules arranged opposite to each other, and a pair of γ photons corresponding to the annihilation event may be respectively detected by the two detector modules arranged opposite to each other on the LOR. Each coincidence event detected by the PET detector may correspond to one LOR, which may be recorded by serial number of the two detector modules corresponding to the LOR, a radial distance r of the LOR, and an angle φ between the LOR and the y-axis. After a PET scanning, many coincidence events may be obtained. All coincidence events may be arranged according to the angles φ and radial distances r of the LORs of the coincidence events to form a matrix diagram, i.e., a raw data sinogram (referred to as sinogram for short). A pixel value on the sinogram may be a count of coincidence events corresponding to the position.

A sinogram without Time of Flight information may be called a non-TOF sinogram. A sinogram with the Time of Flight information may be called a TOF sinogram. In traditional PET technology, when a pair of γ photons is detected within a preset coincidence event window, an annihilation time may be considered to occur. A specific position of the annihilation event in the LOR may merely be determined through image reconstruction. Since there is no other information provided, a reconstruction algorithm may assume that probabilities of annihilation events occurring at all positions on the LOR are the same when performing initial reconstruction, i.e., contribution of each point on the LOR is the same, and a count of annihilation events on each LOR may be obtained by counting the annihilation events by LOR. The reconstruction process may be called non-TOF reconstruction, and the non-TOF reconstruction may not consider the Time of Flight. For a LOR, each time a coincidence event corresponding to the LOR is detected, in the non-TOF sinogram, the count of coincidence events corresponding to each pixel on the LOR may be increased by 1, so the count of coincidence events corresponding to each pixel in the non-TOF sinogram may be large, and statistics may be guaranteed when the count is large enough.

With improvement of a time resolution of the PET detector, a time difference (also referred to as Time of Flight (TOF) or Time of Flight value, i.e., TOF value) between a pair of γ photons arriving at the two detector modules arranged opposite to each other. The farther the annihilation position is from a center of the LOR, the greater the time difference between the pair of γ photons arriving at two detector modules arranged opposite to each other. According to the Time of Flight, the annihilation position of the annihilation event may be determined theoretically. If the time resolution of the detector is high, i.e., the Time of Flight is accurate enough (e.g., accurate to 1 picosecond or 1 femtosecond), the annihilation position of the annihilation event may be determined directly from the Time of Flight for PET image reconstruction. But in fact, the time resolution of the detector is limited, so the Time of Flight may only be accurate to an order of hundreds of picoseconds, so the determined annihilation position of the annihilation event may not be an exact point, but may only be limited to within a certain range centered on the point. However, the reconstruction process may still be constrained based on a certain range. The annihilation position may be preliminarily determined within the certain range, and a reasonable weight probability distribution may be made for the reconstruction information of the coincidence event. In this way, only voxels near a real annihilation position contributes to a projection value during reconstruction, so a count of voxels involved in the calculation may be reduced, and a degree of contribution of each voxel to the projection value may be calculated reasonably. In some embodiments, the reconstruction process may be referred to as TOF reconstruction.

The network 120 may include any suitable network that facilitates the exchange of information and/or data for the imaging system 100. In some embodiments, one or more components of the imaging system 100 (e.g., the imaging device 110, the terminal 130, the processing device 140, the storage 150) may communicate information and/or data with one or more other components of the imaging system 100 through the network 120. For example, the processing device 140 may obtain the PET scan data from the imaging device 110 through the network 120. In some embodiments, the processing device 140 may obtain a user instruction from the terminal 130 through the network 120.

The terminal 130 may include a mobile device 131, a tablet computer 132, a laptop computer 133, or the like, or any combination thereof. In some embodiments, the terminal 130 may be a part of the processing device 140. In some embodiments, the terminal 130 may be used to input the user instruction, display a scan result (e.g., reconstructed medical image), etc. In some embodiments, the terminal 130 may issue prompt information to remind the user. In some embodiments, the terminal 130 may be used to display image information (e.g., a PET image, a PET-CT image, a PET-MR image).

The processing device 140 may process the data and/or information obtained from the imaging device 110, the terminal 130, and/or the storage 150. In some embodiments, the processing device 140 may obtain radiation events. The processing device 140 may determine first response information based on the radiation events. The processing device 140 may determine second response information based on the radiation events. The processing device 140 may generate an image (also referred to as a first image) based on the updated second response information.

The storage 150 may store the data, the instruction, and/or any other information. In some embodiments, the storage 150 may store data obtained from the terminal 130 and/or the processing device 140. In some embodiments, the storage 150 may store the data and/or the instruction, the processing device 140 and/or terminal 130 may execute or use the data and/or the instruction to implement the exemplary method described in the present disclosure. In some embodiments, the storage 150 may be connected to the network 120 to communicate with one or more other components (e.g., the processing device 140, the terminal 130) of the imaging system 100. The one or more components of the imaging system 100 may access the data or the instruction stored in the storage 150 via the network 120. In some embodiments, the storage 150 may be directly connected to or in communication with the one or more other components (e.g., the imaging device 110, the processing device 140, the terminal 130) of the imaging system 100. In some embodiments, the storage 150 may be a part of the processing device 140.

FIG. 2 is a flowchart illustrating an exemplary process for medical imaging according to some embodiments of the present disclosure. In some embodiments, the process 200 may be executed by the processing device 140. For example, the process 200 may be stored in a storage device (e.g., a self-contained storage unit of the processing device or an external storage device) in the form of a program or an instruction. When the program or instruction is executed, the process 200 may be implemented. In some embodiments, the process 200 may include the following operations.

In 210, radiation events may be obtained. In some embodiments, the operation 210 may be performed by a radiation event obtaining module 1110.

In some embodiments, the processing device may detect the radiation events from an imaging region of an object by a plurality of detection units of an imaging device The object may be biological or abiological. Merely by way of example, the object may include a patient, a man-made object (e.g., a man-made model), and so on.

The imaging region refers to a scanning area/detection region of the detection unit of the imaging device. In some embodiments, the imaging region may be a part of the object, e.g., a specific part, an organ, and/or a tissue thereof.

In some embodiments, the radiation events may also be referred to as raw data obtained by scanning. The raw data refers to PET scan data obtained by the imaging device 110 (e.g., a PET device) by performing a PET scanning on the object (e.g., the patient). For example, the imaging device 110 may obtain the raw data of the object by performing a continuous scanning on the object. Data of several periods of time may be obtained by scanning. As another example, the imaging device 110 may include a PET detector. The PET detector may include a plurality of detector modules (referred to as "detection units") that detect gamma photons (γ photons) to obtain the raw data of the object. The plurality of detection units may be arranged to form one or more detection rings. In some embodiments, the raw data may include a count of radiation events and/or Time of Flight information on lines of response associated with the plurality of detection units.

More descriptions regarding the radiation events may be found in FIG. 1 and the related descriptions thereof.

In 220, first response information may be determined based on the radiation events. In some embodiments, the operation 220 may be performed by a first response information determination module 1120.

In some embodiments, the processing device may generate a second image based on the radiation events and determine the first response information based on the second image.

The second image refers to an obtained image that roughly reflects an object contour of the object. For example, the second image may be an image including the tissue/organ contour of the object obtained through image reconstruction based on the radiation events.

In some embodiments, the processing device may reconstruct and obtain the second image in various ways. For example, the second image may be reconstructed and obtained in a way such as an image reconstruction, a rearrangement, a machine learning-based process, etc. The present disclosure may not limit the specific way of reconstructing the second image.

For example, the processing device may obtain a time-covered image (histo-image), i.e., the second image, by performing an operation such as sorting, grouping, and mapping on the radiation events according to the time information. In some embodiments, the second image may be also referred to as an initial image of the object. Exemplarily, the process of reconstructing the second image based on the radiation events may be as shown in the following embodiments.

First, the processing device may perform preliminary processing on data (e.g., energy calibration, time calibration) of the radiation event. Afterwards, the processing device may generate a plurality of time slices by sorting and grouping the processed radiation events according to the time information. For each time slice, the radiation events may be mapped into a spatial coordinate system in a PET imaging system, and energy deposition may be converted into photon signals using a technique such as a scintillator. In the PET imaging system, the photon signals may be detected and recorded using a detector array and an electronics processor. At the end of each time slice, a count value may be accumulated at a position corresponding to a PET image according to the recorded photon signal position and time information. By accumulating the count values in all time slices, the histo-image may be obtained. Each pixel value representing a count of photon signals may be recorded at the position.

In some embodiments, the radiation events may further include first radiation events, and each of the first radiation events may have a corresponding Time of Flight. The first radiation event may be a radiation event normally detected by the detector module of the imaging device.

For each first radiation event of the first radiation events, the processing device may determine an ideal annihilation position according to a Time of Flight corresponding to the first radiation event. The processing device may obtain a broadened annihilation position by broadening the ideal annihilation position, and generate the second image based on the broadened annihilation positions.

The ideal annihilation position refers to a theoretical position where the radiation event occurs. When being annihilated in the object, two positrons may emit two gamma photons of equal energy and opposite directions. The two gamma photons may pass through an array of crystals that consists of the PET detector, one gamma photon may be detected on one of the crystals, while the other gamma photon may be detected on the other crystal. Position information of the two gamma photons on the PET detector and times when the PET detector detects the gamma photons (i.e., Time of Flight) may be recorded. According to the Time of Flight and a geometric structure of the PET detector, a possible position where the two gamma photons possibly annihilated in the PET detector may be calculated, and the position may be the ideal annihilation position.

Broadening may be used to reduce influence of a line of response corresponding to an anomaly detection unit on determining the Time of Flight. When the radiation events are detected, considering the impact of a time resolution of the PET device, broadening when the position of the annihilation event is determined based on a Time of Flight difference may improve the accuracy of determining the position of the radiation event. Because the position of the radiation event obtained based on the Time of Flight difference and the resolution is within a certain range, an accurate position may be obtained by broadening (e.g., a position may be randomly determined as the position of the radiation event within a range based on the Gaussian distribution).

In some embodiments, the broadening may include a Gaussian broadening, a cubic spline interpolation broadening, a Fourier transform broadening, etc.

In some embodiments, the processing device 140 may generate the image based on the first radiation event of which the ideal annihilation position is determined.

In some embodiments, the generating the second image may be implemented by the rearrangement described above or other manners. The present disclosure may not limit the manner of generating the second image.

Response information refers to various types of information related to occurrence of radiation events and a count of radiation events. For example, the response information may include information such as the count of radiation events on the line of response and counts when the radiation events occur. In some embodiments, the response information may also be referred to as a sinogram. The sinogram may be an image obtained according to the count of radiation events on each line of response actually detected by the detection unit. A gray value of each pixel on the sinogram reflects the count of radiation events collected on the pixel. The greater the count of radiation events, the greater the gray value of the pixel.

In some parts of the present disclosure, the sinogram may be used as an alternative name for the response information. The sinogram may be in the form of a diagram or any other form of data. Information of several lines of response may be included in the response information. The line of response refers to a connecting line consisting of two detector positions. Each detector position may be a position of one detector or a position of an adjacent group of detectors. The information of the line of response may include information of events received by the corresponding detector. The information may include position information, energy deposition information, time information, negative positive information of gamma rays, etc. Since the PET detector may usually have an array structure, the negative positive information may refer that whether gamma photons enter from the front or back of the PET detector.

The first response information refers to the response information determined based on the second image.

In some embodiments, the first response information may include first time information of the radiation events. The first time information may be the Time of Flight difference of the radiation events detected by the detection unit on the line of response. The Time of Flight difference refers to a time difference between two gamma photons being detected by the detector at the same time when simultaneously annihilated in a body.

In some embodiments, the first response information may include a count of first coincidence events on a line of response corresponding to at least one anomaly detection unit. The first time information may be Time of Flight information related to the line of response corresponding to the at least one anomaly detection unit.

The second image may reflect the count of radiation events corresponding to the pixel to a certain extent by the gray value of the pixel, but the time information may not be directly obtained from the second image, so it may be necessary to obtain relevant time information by determining based on the second image and obtain the first response information. In some embodiments, it may be carried out based on the second image in a dimension of the Time of Flight. For example, sinograms may be calculated for different Time of Flight differences. For example, radiation events of the Time of Flight difference of 0 may be drawn on a graph, radiation events of the Time of Flight difference of 100 picoseconds may be drawn on a graph, and radiation events of the Time of Flight difference of 200 picoseconds may be drawn on a graph. By analogy, distribution of Time of Flight differences on each line of response may be obtained, i.e., a count of radiation events of the Time of Flight difference on the line of response of 0, a count of radiation events of the Time of Flight difference of 100 picoseconds, a count of radiation events of the Time of Flight difference of 200 picoseconds, and then the first response information may be determined. The determining the first response information may be understood as a reasoning calculation of the first response information, which may be subjective and not necessarily practical.

In some embodiments, the processing device may determine the first response information in other ways, for example, the processing device may obtain a forward projection result by performing a forward projection on the second image, and determining the first response information based on the forward projection result. In some embodiments, the forward projection result may also be referred to as a third sinogram.

The forward projection may be also referred as to an orthographic projection, and the process of the forward projection may be a process of projecting the second image from an image domain to a data domain. The second image may reflect a spatial distribution of a tracer (e.g., fluoroglucose) metabolism in the object, and the sinogram corresponding to the data of the radiation event collected by the PET detector may be calculated mathematically. For example, the processing device 140 may project the second image from the image domain to the data domain according to the following equation (1):

$$y_i = \Sigma_j P_{ij} \tilde{x}_j \qquad (1)$$

where $y_i$ denotes a value of an $i^{th}$ element ($i^{th}$ line of response) in the projection result, $P_{ij}$ denotes a value of a system matrix for a $j^{th}$ image element (voxel) and $i^{th}$ element of the initial image, and $\tilde{x}_j$ denotes a value of a $j^{th}$ element of the second image. The system matrix reflects contribution of the second image to the line of response, i.e., the distribution of probability positron annihilation on the second image.

The corresponding first response information may be obtained according to the distribution of the probability positron annihilation on the second image.

In 230, second response information may be determined based on the radiation events. In some embodiments, the operation 230 may be performed by a second response information determination module 1130.

The second response information may include response information corresponding to an anomaly detection unit and lack time information. Different from the first response information, the image reconstruction involved in the determination process of the first response information may be TOF reconstruction, i.e., the TOF may be added in the reconstruction process, while the response information corresponding to the anomaly detection unit in the second response information may lack time information. The response information corresponding to the anomaly detection unit lacking the time information refers to that the response information corresponding to the anomaly detection unit does not include the time information.

The line of response corresponding to the anomaly detection unit may be a line of response to which the detector corresponding is defective. The defect here may include detector damage, abnormal detection of radiation events, etc. For example, the detector damage may include crystal crack or breakage, photomultiplier tube damage, cable failure, mechanical structure looseness, high voltage supply failure, etc. In some embodiments, the defective detector may also be referred to as the anomaly detection unit.

The response information corresponding to the anomaly detection unit refers to response information with relatively weak accuracy, or the response information corresponding to the anomaly detection unit refers to less accurate response information. Whether the response information is accurate as a relative concept may depend on an object of comparison. For example, response information of a line of response corresponding to a normal detector may be regarded as the accurate response information, and response information of a line of response corresponding to the defective detector may be regarded as the response information corresponding to the anomaly detection unit.

In some embodiments, the response information corresponding to the anomaly detection unit may include a count of radiation events on a line of response corresponding to the anomaly detection unit. Since the detector corresponding to the line of response corresponding to the anomaly detection unit is defective, it may not be possible to accurately detect the occurrence of the radiation events and obtain the corresponding TOF when the detector is defective. The calculation of the TOF information may depend on accurate measurement of the line of response, so when a detector on a line of response is damaged, it may be difficult to recover the TOF information of the line of response. Especially when a time-oriented reconstruction algorithm is used, since the TOF information of each line of response needs to be calculated accurately, the response information corresponding to the anomaly detection unit may lack the time information.

In some embodiments, the response information corresponding to the anomaly detection unit may be determined according to a data repair process based on the radiation events.

The data repair process refers to a process of supplementing missing data or correcting inaccurate data. For example, for the line of response corresponding to the anomaly detection unit, the count of radiation events may be smaller than that of radiation events that actually occur since the detector is defective, and the data repair process may supplement the count of missing radiation events.

In some embodiments, the processing device may perform the data repair process by means of an interpolation process or based on a deep learning process. Exemplarily, the data repair process may be as shown in the following embodiments.

In some embodiments, the processing device may obtain initial response information based on the radiation events and determine the second response information by performing the data repair process on the initial response information.

The initial response information refers to response information determined directly based on the radiation events. In some embodiments, the initial response information may be response information obtained based on the rearrangement of the radiation events. In some embodiments, the initial response information may also be referred to as a first sinogram.

In some embodiments, the processing device may calculate positions (i.e., positron annihilation position), where positrons and gamma photons are annihilated in the body based on the detected position information of the positrons and gamma photons in the radiation events. A "distance matrix" may be obtained by sorting relative distances between all the positron annihilation positions in ascending order. Two-dimensional or three-dimensional data space may be obtained by performing image processing on the distance matrix. For example, the dimensionality of data may be reduced by using a multi-dimensional dimensionality reduction technique such as a traditional Multidimensional Scaling (MDS) manner, an Isomap manner. Each positron annihilation position in the data space may be taken as a node, a straight line may be connected between different nodes, and a sinogram without TOF (i.e., the initial response information) may be generated.

In some embodiments, the processing device may also obtain the initial response information in other ways. For example, the processing device may obtain the initial response information using a reconstruction algorithm. The present disclosure may not limit the specific manner for obtaining the initial response information.

The data repair process of the initial response information may be achieved by means of an interpolation process, or a deep learning process, or other ways. More descriptions regarding the data repair process may be found elsewhere in the present disclosure, e.g., FIG. 5 and the related descriptions thereof.

In some embodiments, the processing device may use the response information after the data repair process as the second response information. In some embodiments, the second response information may also be referred to as a second sinogram.

The second time information refers to Times of Flight of radiation events in estimated response information corresponding to the anomaly detection unit.

In some embodiments, the processing device may determine a correspondence between the radiation events and the Times of Flight in the first response information based on the first time information. For example, the correspondence may include how many radiation events correspond to each Time of Flight. The second time information may be allocated to the response information corresponding to the anomaly detection unit.

More descriptions regarding the allocating the second time information may be found in FIG. 3 and the related descriptions thereof. In some embodiments, the second time information may be a first Time of Flight value of the first coincidence event on the line of response corresponding to the at least one anomaly detection unit.

In 240, an image (also referred to as a first image) may be generated based on the first response information and the second response information. In some embodiments, the operation 240 may be performed by an image generation module 1140.

In some embodiments, for the response information corresponding to the anomaly detection unit, the processing device may obtain updated second response information by allocating second time information to the response information based on the first time information; and generate the image based on the updated second response information.

The updated second response information refers to second response information after missing time information in the response information corresponding to the anomaly detection unit is supplemented. In some embodiments, it may also be understood that the response information corresponding to the anomaly detection unit in the updated second response information includes the second time information. As mentioned above, the missing time information may be supplemented by allocating the second time information to the response information corresponding to the anomaly detection unit based on the first time information.

The image (also referred to as the first image) refers to a medical image to be obtained. For example, the image may be a PET image without artifacts to be obtained by performing the PET scanning. In some embodiments, the image may also be referred to as a Positron Emission Tomography (PET) image of the object.

In some embodiments, the processing device may generate the image (also referred to as the first image) using a traditional image reconstruction algorithm based on the updated second response information. In some embodiments, the processing device may perform the image reconstruction using different reconstruction algorithms, including an analytical reconstruction algorithm or an iterative reconstruction algorithm. An exemplary analytical reconstruction algorithm may include a filtered back projection (FBP) algorithm, a back projection filtered (BFP) algorithm, a p filtering algorithm, or the like, or any combination thereof. An exemplary iterative reconstruction algorithm may include a Maximum Likelihood Expectation Maximization (ML-EM) algorithm, an Ordered Subset Expectation Maximization (OSEM) algorithm, a Row Processing Maximized Likelihood (RAMLA) algorithm, a Dynamic Row Processing Maximizing Likelihood (DRAMA) algorithm, or the like, or any combination thereof.

The processing device may also perform the image reconstruction using other manners, e.g., a deep learning process, etc. The present disclosure may not limit the specific manner of image reconstruction.

In some embodiments of the present disclosure, the second image may be reconstructed based on the radiation events. The first response information including the first time information may be determined based on the second image. The second response information may be determined according to the data repair process, the second response information including the response information lacking time information corresponding to the anomaly detection unit, and the updated second response information may be obtained by supplementing the lacking time information on the line of response corresponding to the anomaly detection unit in the response information corresponding to the anomaly detection unit based on the first response information. In the updated second response information, since both the radiation events and the time information on the line of response corresponding to the anomaly detection unit corresponding to a defective detector are repaired (the radiation event is determined according to the data repair process, and the time information may be obtained by allocating based on the first time information), so that a high-quality medical image without artifacts may be reconstructed, and quantification of the image may be also accurate.

FIG. 3 is a flowchart illustrating an exemplary process for allocating second time information to response information corresponding to an anomaly detection unit according to some embodiments of the present disclosure. In some embodiments, the process 300 may be performed by the processing device 140. For example, the process 300 may be stored in a storage device (e.g., a self-contained storage unit of the processing device or an external storage device) in the form of a program or an instruction. When the program or instruction is executed, the process 300 may be implemented. In some embodiments, the process 300 may include the following operations.

For one line of response corresponding to the anomaly detection unit, the processing device may obtain updated second response information by allocating second time information to the response information based on the first time information by performing the operations 310 to 330.

In 310, a time distribution of a reference line of response may be determined based on the first time information of the first response information.

The reference line of response refers to a line of response corresponding to the anomaly detection unit.

In some embodiments, there may be one or more reference lines of response. For example, if a plurality of detector modules are defective, there may be a plurality of lines of response corresponding to the anomaly detection unit, and accordingly there may be a plurality of reference lines of response.

The reference line of response may be determined based on a count of radiation events on each line of response in the first response information. For example, when reconstructing the second image based on one radiation event, a theoretical annihilation position of the radiation event may be calculated according to the time information of the radiation event, ignoring influence of a time resolution of the detector. Assuming that the radiation event occurs at the theoretical annihilation position, the second image may be obtained by performing the same processing on all the radiation events. Although data of the line of response corresponding to the defective detector may be missing, lines of response corresponding to other normal detectors may also pass through a position on the line of response (line of response corresponding to the anomaly detection unit) corresponding to the defective detector, and there may also be data on the line of response corresponding to the line of response corresponding to the anomaly detection unit on the second image, and an amount of the data may be smaller than that on other normal lines of response. Therefore, the processing device may determine the reference line of response in the first response information based on the position of the defective detector or determine the reference line of response based on the amount of the data on each line of response in the first response information.

The reference line of response has a position correspondence relationship with the line of response corresponding to the anomaly detection unit. The position correspondence relationship refers that a position of the reference line of response in the first response information is the same as a position of the line of response corresponding to the anomaly detection unit in the second response information.

In some embodiments, a reference line of response may correspond to one or more lines of response corresponding to the anomaly detection unit. The second response information may be obtained after a data repair process is performed on the radiation events, and the second response information may be a very clear and correct acquisition image. Although the first response information is more coarsely visualized than the second response information, there may also be data on the reference line of response corresponding to the line of response corresponding to the anomaly detection unit.

Since a plurality of lines of response are compressed and merged into one thick line of response to make a sinogram when obtaining the second response information, the purpose may be to facilitate the data repair process in the dimension when a count of radiation events on each line of response is sufficient to obtain a good data repair effect. The first response information may be obtained by performing a forward projection on the second image, and the second image may merely reflect a blurred contour. Therefore, even at one same accuracy level (e.g., grp4-level), there may be no one-to-one correspondence between the first line of response in the first response information and the line of response in the second response information, so a reference line of response in the first response information may correspond to one or more lines of response corresponding to the anomaly detection unit in the second response information.

The accuracy level reflects a size or accuracy of the sinogram (response information). The higher the accuracy level, the smaller the size of the sinogram, the greater the calculation speed, the smaller the noise, and the smoother, finer, and flatter the image.

In some embodiments, the accuracy level of the obtained first response information and the accuracy level of the obtained second response information may be adjustable. For example, both the accuracy level of the first response information and the accuracy level of the second response information may be grp4-level, grp2-level, etc.

The accuracy level of the first response information and the accuracy level of the second response information may be adjusted, so that the line of response in the first response information may correspond to the line of response in the second response information accurately, so as to determine a specific position of each line of response as accurately as possible, and then reconstruct a high-quality medical image.

The time distribution refers to statistical information of Time of Flight values of the radiation events in the first response information. In some embodiments, the time distribution may include a distribution of Time of Flight differences in different periods of time.

The different periods of time may refer to periods of time consisting of different Time of Flight differences. Each period of time may include a plurality of Time of Flight differences. For example, a Time of Flight difference of 10 picoseconds-50 picoseconds may correspond to a period of time, a Time of Flight difference of 60 picoseconds-100 picoseconds may correspond to a period of time, etc. An interval length of the period of time may be determined according to an actual situation. For example, a single Time of Flight difference, e.g., 200 picoseconds, may be used as a period of time, which is not limited in the present disclosure.

In some embodiments, the processing device may determine the time distribution of the reference line of response by counting and recording the Time of Flight of each radiation event on the reference line of response. For example, there may be 50 Time of Flight differences of 0 picoseconds-10 picoseconds; there may be 30 Time of Flight differences of 10 picoseconds-50 picoseconds; and there may be 20 Time of Flight differences of 50 picoseconds-100 picoseconds, etc.

The time distribution may help to understand a time resolution and performance of a PET imaging system. For example, if the distribution is relatively concentrated, it may mean that the time resolution of the PET imaging system may be relatively high and an arrival time of gamma photons may be accurately detected. On the contrary, if the distribution is relatively scattered, it may mean that the time resolution of the PET imaging system is relatively low, or there may be other interference factors. When the time distribution is relatively scattered, a re-scan of the object may be considered to obtain high-quality scanned data.

In 320, a total count of radiation events on the line of response corresponding to the anomaly detection unit may be determined.

In some embodiments, the processing device may determine the total count of radiation events on the line of response corresponding to the anomaly detection unit by counting a count of radiation events on the line of response corresponding to the anomaly detection unit. For example, the total count of radiation events on the line of response corresponding to the anomaly detection unit may be 100, 200, 500, etc.

In some embodiments, the total count of radiation events may be a total count of radiation events on a single line of response corresponding to the anomaly detection unit.

In 330, the second time information may be allocated to the response information corresponding to the anomaly detection unit based on the time distribution and the total number of radiation events on the line of response corresponding to the anomaly detection unit.

In some embodiments, the processing device may directly determine a proportion of allocating to the radiation events on the line of response corresponding to the anomaly detection unit based on the time distribution, and allocate the second time information to the radiation events on the line of response corresponding to the anomaly detection unit according to the proportion. For example, if there are 500 Times of Flight in total, there are 100 Times of Flight in a first period of time, there are 200 Times of Flight in a second period of time, and there are 200 Times of Flight in a third period of time, an allocation proportion of the Times of Flight may be 1:2:2. When time allocation is performed on the radiation events according to the proportion, the time information may be allocated to each radiation event according to the proportion. For example, for a first radiation event, the Times of Flight in the first period of time may be allocated, for a second radiation event and a third radiation event, the Times of Flight in the second period of time may be allocated, for a fourth radiation event and a fifth radiation event, the Times of Flight in the third period of time may be allocated, and loop may be executed with five radiation events as one round until the time information is allocated to each radiation event.

It should be noted that the above example is merely for the purpose of illustration and roughly describes the manner of allocating the second time information to the response information corresponding to the anomaly detection unit, which is not intended to limit the specific allocation manner. For example, allocation may not necessarily need to be performed strictly according to the allocation proportion and may also be performed in other ways. For example, for each radiation event on the line of response corresponding to the anomaly detection unit, the processing device may determine the Time of Flight based on a period of time, which may be any period of time in the time distribution. When determining the Time of Flight based on the period of time, the processing device may directly use the Time of Flight in the period of time (assuming there is only one Time of Flight in the period of time) as the second time information (Time of Flight) of the radiation event, or the processing device may randomly select a Time of Flight in the period of time (assuming that there are a plurality of Times of Flight in the period of time) as the second time information of the radiation event.

In some embodiments, the processing device may also convert the time distribution into a probability distribution. The probability distribution may be configured to reflect a probability of allocating a certain period of time to each radiation event on the line of response corresponding to the anomaly detection unit.

Based on the probability distribution, the processing device may allocate the period of time to each radiation event on the line of response corresponding to the anomaly detection unit by means of probability density sampling or random probability and determine the Time of Flight based on the allocated period of time.

The second time information may be allocated to the radiation events on the line of response corresponding to the anomaly detection unit by means of probability density sampling, which may be equivalent to performing a random sampling on each radiation event, so that the determined second time information may have randomness. If the manner of random probability is directly used, for example, 50% radiation events may be directly randomly allocated with the Time of Flight difference of 100 picoseconds, 20% radiation events may be directly randomly allocated with the Time of Flight difference of 200 picoseconds, the calculation speed may be fast, and the reconstructed PET image may be obtained quickly, thereby reducing waiting time of a user.

FIG. 4 is a flowchart illustrating an exemplary process for positron emission tomography according to some embodiments of the present disclosure. In some embodiments, the process 400 may be performed by the processing device 140. For example, the process 400 may be stored in a storage device (such as a self-contained storage unit of the processing device or an external storage device) in the form of a program or an instruction. When the program or instruction is executed, the process 400 may be implemented. In some embodiments, the process 400 may include the following operations.

In 410, raw data of an object may be obtained. In some embodiments, the operation 410 may be performed by an obtaining module 1210.

The raw data herein refers to PET scan data obtained by the imaging device 110 (e.g., a PET device) by performing a PET scanning on the object (e.g., a patient). For example, the imaging device 110 may obtain the raw data of the object by performing a continuous scanning on the object, i.e., data of several periods of time may be obtained by scanning. As another example, the imaging device 110 may include a PET detector. The PET detector may include a plurality of detector modules (referred to as "detection units"). The plurality of detector modules may obtain the raw data of the object by detecting gamma photons (γ photons). The plurality of detection units may be arranged to form one or more detection rings. In some embodiments, the raw data may include a count of coincidence events and/or Time of Flight information on lines of response associated with the plurality of detection units. In some embodiments, the plurality of detection units may include at least one anomaly detection unit. The anomaly detection unit refers to a damaged or failed detection unit (also refer to as a "bad channel"). The counts collected by the anomaly detection unit on the relevant lines of response (LOR) associated with the anomaly detection unit may be abnormal. For example, the counts may not be collected or the collected counts may be inaccurate. Therefore, the anomaly detection unit may cause the raw data to include abnormal data obtained by the at least one anomaly detection unit detecting γ photons.

In some embodiments, the processing device 140 may obtain the raw data of the object directly from the imaging device 110. In some embodiments, the processing device 140 may obtain the raw data of the object from the storage 150.

In 420, a count of first coincidence events on a line of response corresponding to the at least one anomaly detection unit may be estimated according to the raw data. In some embodiments, the operation 420 may be performed by a count estimation module 1220.

Since the plurality of detection units of the PET detector include the at least one anomaly detection unit, the raw data may include a count of coincidence events on a line of response associated with a normal detection unit and an anomaly count of coincidence events (referred to as the first coincidence events) on a line of response associated with anomaly detection units. The anomaly count may be zero or has a small probability of non-zero.

In some embodiments, the processing device 140 may obtain a first sinogram of the object based on the raw data and obtain a second sinogram by performing an interpolation and/or a deep learning process on the first sinogram, so as to estimate a count of first coincidence events on a line of response corresponding to the at least one anomaly detection unit, thereby repairing the anomaly count of first coincidence events on the line of response corresponding to the at least one anomaly detection unit in the raw data. More descriptions regarding repairing the anomaly count may be found elsewhere in the present disclosure (e.g., FIG. 5 and the related descriptions thereof).

In 430, TOF information related to the line of response corresponding to the at least one anomaly detection unit may be estimated according to the raw data. In some embodiments, the operation 430 may be performed by a TOF information estimation module 1230.

Since the at least one anomaly detection unit is a damaged or failed detection unit, the anomaly detection unit may not detect the TOF information of the first coincidence events on the line of response related to the at least one anomaly detection unit (e.g., times when a pair of $\gamma$ photons corresponding to the first coincidence event are detected by detection units arranged opposite to each other) or the TOF information of the first coincidence event may be inaccurate, so that the raw data may include TOF information related to the line of response corresponding to the normal detection unit, but may not include TOF information related to the line of response corresponding to the at least one anomaly detection unit or include anomaly TOF information related to the line of response corresponding to the at least one anomaly detection unit.

In some embodiments, the processing device 140 may obtain an initial image of the object through TOF reconstruction based on the raw data, generate a third sinogram by performing a forward projection on the initial image, and estimate the TOF information related to the line of response corresponding to the at least one anomaly detection unit based on the third sinogram. The TOF information may include a distribution (e.g., a proportion of coincidence events with different Time of Flight differences to a total count of coincidence events) of Time of Flight differences (i.e., TOF values) of coincidence events on the lines of response corresponding to the plurality of detection units. Both the first sinogram and the second sinogram may be sinograms that do not include the TOF information, i.e., non-TOF sinograms. The third sinogram may be a sinogram including TOF information, i.e., a TOF sinogram. The first sinogram (or the second sinogram) and the third sinogram may have different accuracy levels. For example, the first sinogram (or the second sinogram) may correspond to a first accuracy level, and the third sinogram may correspond to a second accuracy level. The first accuracy level may be greater than the second accuracy level, i.e., the third sinogram may be a relatively rough sinogram, and the second sinogram may be a relatively clear and accurate sinogram. In some embodiments, a pixel of the first sinogram (or the second sinogram) and a pixel of the third sinogram may be accurate to a same level (e.g., centimeter level). For example, both the first sinogram (or the second sinogram) and the third sinogram may be grp4-level sinograms. More descriptions regarding estimating the TOF information may be found elsewhere in the present disclosure (e.g., FIG. 6 and the related descriptions thereof).

In 440, first TOF values of the first coincidence events on the line of response corresponding to the at least one anomaly detection unit may be estimated according to the TOF information. In some embodiments, the operation 440 may be performed by a TOF value estimation module 1240.

As mentioned above, there may be a difference in the accuracy levels between the second sinogram and the third sinogram, so the third sinogram may not be accurately mapped to the second sinogram. For example, second coincidence events on the line of response corresponding to the at least one anomaly detection unit in the third sinogram may not be in a one-to-one correspondence with the first coincidence events on the line of response corresponding to the at least one anomaly detection unit in the second sinogram. For example, a count of second coincidence events in the third sinogram may be 100, and a count of first coincidence events in the second sinogram may be 98. In some embodiments, the processing device 140 may determine the first TOF value corresponding to each first coincidence event by performing probability density sampling on each first coincidence event according to the TOF information estimated in the operation 430. More descriptions regarding the estimating the TOF values may be found elsewhere in the present disclosure (e.g., FIG. 7 and the related descriptions thereof).

In 450, a PET image of the object may be generated according to the raw data and the first TOF values of the first coincidence events. In some embodiments, the operation 450 may be performed by a reconstruction module 1250.

In some embodiments, the processing device 140 may generate a fourth sinogram based on the first TOF values of the first coincidence events and the raw data. For example, the processing device 140 may obtain the TOF values of the coincidence events on the line of response corresponding to the normal detection unit according to the raw data. The processing device 140 may obtain the estimated first TOF values of the first coincidence events on the line of response corresponding to the at least one anomaly detection unit obtained according to the operation 440. The processing device 140 may obtain the count of coincidence events on the line of response corresponding to the normal detection unit and an estimated count of first coincidence events on the line of response corresponding to the at least one anomaly detection unit according to the second sinogram. The fourth sinogram may be the repaired TOF sinogram, including the count and TOF values of the coincidence events on the line of response corresponding to the normal detection unit and an estimated count of the first coincidence events on the line of response corresponding to the at least one anomaly detection unit and estimated first TOF values. The processing device 140 may generate a fifth sinogram by rearranging the fourth sinogram according to a PET reconstruction requirement. A pixel of the fifth sinogram and a pixel of the fourth sinogram may be accurate to different levels. For example, the fourth sinogram may be a sinogram accurate to a centimeter level, and the fifth sinogram may be a sinogram accurate to a millimeter level. As another example, the fourth sinogram may be a grp4-level sinogram, and the fifth sinogram may be a grp2-level sinogram. In some embodiments, the processing device 140 may generate list data by rearranging the fourth sinogram.

Further, the processing device 140 may generate the PET image of the object by performing image reconstruction based on the fifth sinogram or list data. In some embodiments, image reconstruction may be performed using different reconstruction algorithms, including an analytical reconstruction algorithm or an iterative reconstruction algorithm. An exemplary analytical reconstruction algorithm may include a filtered back projection (FBP) algorithm, a back projection filtered (BFP) algorithm, a p filtering algorithm, or the like, or any combination thereof. An exemplary iterative reconstruction algorithm may include a Maximum Likelihood Expectation Maximization (ML-EM) algorithm, an Ordered Subset Expectation Maximization (OSEM) algorithm, a Row Processing Maximized Likelihood (RAMLA) algorithm, a Dynamic Row Processing Maximizing Likelihood (DRAMA) algorithm, or the like, or any combination thereof.

In some embodiments of the present disclosure, thanks to the improvement of a time characteristic of the PET system, the initial image of the object may be directly obtained through a reconstruction algorithm that directly "puts back" the time at a position corresponding to the line of response according to the Time of Flight difference (TOF value). image. A guessed (or estimated) detector response sinogram (TOF sinogram) with the TOF information may be obtained by performing the forward projection on the initial image, combined with the detector response sinogram (non-TOF sinogram) without the TOF information obtained by sinogram repair, all information (including the count of coincidence events and the TOF values of the coincidence events) of the events on the line of response corresponding to the failure detector module may be completely recovered, so as to perform image reconstruction more accurately. The PET image can still be correctly reconstructed when the detector module of the PET detector is damaged using the method disclosed in the embodiment of the present disclosure, and the quantification and quality of the image can be guaranteed without serious impact (e.g., the accuracy of image quality and image quantification can be ensured within a certain range), which can avoid re-scanning the object to re-collect data, greatly reduce the downtime probability of the PET system, and improve the robustness of the entire PET reconstruction system.

Figure 5:
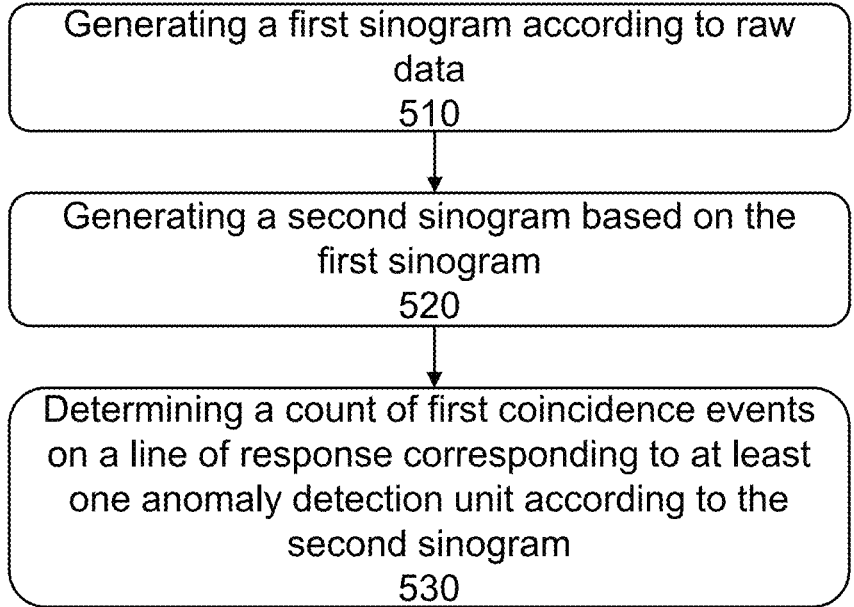
FIG. 5 is a flowchart illustrating an exemplary process for recovering a count of coincidence events on a line of response corresponding to a bad channel (i.e., at least one anomaly detection unit) according to some embodiments of the present disclosure.

FIG. 5 is a flowchart illustrating an exemplary process for recovering a count of coincidence events on a line of response corresponding to a bad channel (i.e., at least one anomaly detection unit) according to some embodiments of the present disclosure.

In some embodiments, the process 500 may be performed by the processing device 140. For example, the process 500 may be stored in a storage device (such as a self-contained storage unit of a processing device or an external storage device) in the form of a program or an instruction. When the program or instruction is executed, the process 500 may be implemented. In some embodiments, the process 500 may include the following operations.

In 510, a first sinogram may be generated according to raw data.

In some embodiments, a count of first coincidence events on the line of response corresponding to the at least one anomaly detection unit in the first sinogram may be abnormal. FIG. 9 are an exemplary bad channel sinogram and an exemplary normal sinogram according to some embodiments of the present disclosure. As shown in FIG. 9, the first sinogram 920 is an exemplary bad channel sinogram, and the first sinogram 920 corresponds to a normal sinogram 910. Compared with the normal sinogram 910, the count of first coincidence events on the line of response corresponding to the at least one anomaly detection unit of the first sinogram 920 may be abnormal, which may be manifested as one or more "black lines" with abnormal counts of zero (or with a small probability of non-zero).

In some embodiments, the first sinogram may be a compressed sinogram. The processing device 140 may directly generate an initial sinogram based on the raw data. The initial sinogram may be a sinogram accurate to a millimeter level, i.e., a pixel of the initial sinogram may be the millimeter level. The processing device 140 may generate the first sinogram by performing compression processing on the initial sinogram. The first sinogram may be a sinogram accurate to a centimeter level, i.e., a pixel of the first sinogram may be the centimeter level. For example, a region of 1 mm×1 mm of the initial sinogram may correspond to one pixel, and a region of 1 cm×1 cm of the first sinogram may correspond to one pixel. One pixel of the first sinogram may correspond to 10×10 (100) pixels of the initial sinogram. The reason why the initial sinogram needs to be compressed may be the count of each pixel at the millimeter level is too small to ensure statistics, so it may be difficult to repair the first coincidence events of the at least one anomaly detection unit, and it may also lead to excessive computation. As another example, the initial sinogram may be a grp2-level sinogram, and the first sinogram may be a grp4-level sinogram.

In 520, a second sinogram may be generated based on the first sinogram.

As mentioned above, the first sinogram may include a count of coincidence events on a line of response corresponding to a normal detection unit and an abnormal count of first coincidence events on the line of response corresponding to the anomaly detection unit, so the abnormal count of first matching events on the line of response corresponding to the anomaly detection unit needs to be repaired. In some embodiments, the processing device 140 may generate the second sinogram by repairing the first sinogram by means of interpolation or base on deep learning. The second sinogram may include an estimated count of first coincidence events on the line of response corresponding to the at least one anomaly detection unit. For example, the first sinogram should be locally smooth based on the assumption that a sinogram of instantaneous coincidence events should be locally smooth. When a proportion of an area of the anomaly detection unit to a total area of a plurality of detection units of the PET detector is relatively small, a lacking part (i.e., a sinogram pixel corresponding to the at least one anomaly detection unit) of the first sinogram may be relatively small accordingly. The processing device 140 may obtain the second sinogram by interpolating count values on normal sinogram pixels around the lacking part of the first sinogram. The second sinogram may include the count value on the sinogram pixel corresponding to the at least one anomaly detection unit (i.e., the count of first coincidence events on the line of response corresponding to the at least one anomaly detection unit). As another example, the processing device 140 may obtain a sinogram repair model corresponding to a current PET detector (e.g., directly obtain a pre-trained sinogram repair model or generate the sinogram repair model through training). The processing device 140 may input the first sinogram into the sinogram repair model so that the sinogram repair model may output the second sinogram. The sinogram repair model may be a machine learning model trained by a deep learning algorithm or an AI algorithm. Merely by way of example, the processing device 140 may obtain a normal sinogram (e.g., a normal sinogram collected and generated when the PET detector does not have an anomaly detection unit). Regions corresponding to part of the detection units in the normal sinogram may be shielded, a large number of abnormal sinograms with failure detection units (i.e., anomaly detection units) may be obtained, the abnormal sinograms and the corresponding normal sinograms may be used as training sets, and the sinogram repair model suitable for a similar situation where the current PET detector fails may be obtained through trained using machine learning model (e.g., convolutional neural network), so that the data can be repaired when the PET detector has the anomaly detection unit.

In 530, the count of first coincidence events on the line of response corresponding to the at least one anomaly detection unit may be determined according to the second sinogram.

In some embodiments, for each anomaly detection unit in the at least one anomaly detection unit, the processing device 140 may take the count of first coincidence events on the line of response corresponding to the anomaly detection unit recovered in the second sinogram as the estimated count of first coincidence events on the line of response corresponding to the anomaly detection unit.

Figure 6:
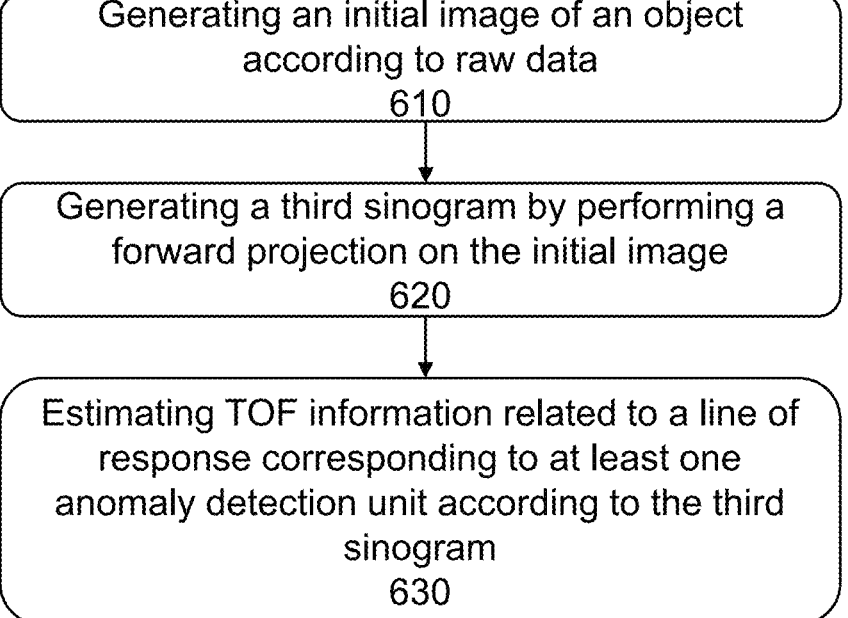
FIG. 6 is a flowchart illustrating an exemplary process for recovering Time of Flight (TOF) information of coincidence events on a line of response corresponding to a bad channel (i.e., at least one anomaly detection unit) according to some embodiments of the present disclosure.

FIG. 6 is a flowchart illustrating an exemplary process for recovering Time of Flight information (i.e., TOF information) of coincidence events on a line of response corresponding to a bad channel (i.e., at least one anomaly detection unit) according to some embodiments of the present disclosure. In some embodiments, the process 600 may be performed by the processing device 140. For example, the process 400 may be stored in a storage device (such as a self-contained storage unit of the processing device or an external storage device) in the form of a program or an instruction. When the program or instruction is executed, the process 400 may be implemented. In some embodiments, the process 400 may include the following operations.

In 610, an initial image (also referred to as histo-image) of an object may be generated according to raw data.

In some embodiments, the processing device 140 may generate the initial image of the object by performing TOF reconstruction based on the raw data. For example, theoretical annihilation positions of coincidence events on a line of response corresponding to a normal detector may be determined according to TOF information of the coincidence events on the line of response corresponding to the normal detector in the raw data, ignoring a time resolution of the detector, so as to generate the initial image. The initial image may be a blurred image, but may reflect a general contour of the object. Although data of the line of response corresponding to the anomaly detection unit may be lacking, a line of response of a normal detection unit may pass through the line of response corresponding to the anomaly detection unit, so there may be data on the line of response corresponding to the anomaly detection unit of the initial image.

In 620, a third sinogram may be generated by performing a forward projection on the initial image.

The process of the forward projection may be a process of projecting the initial image from an image domain to a data domain. The initial image may reflect a spatial distribution of a tracer (e.g., fluoroglucose) metabolism in the object, and the sinogram corresponding to the data of the coincidence event collected by the PET detector may be calculated mathematically. For example, the processing device 140 may generate the third sinogram by projecting the initial image from the image domain to the data domain according to the following equation:

$$y_i = \sum_j P_{ij} \tilde{x}_j,$$

where $y_i$ denotes a value of an $i^{th}$ element (line of response) in the third sinogram, $P_{ij}$ denotes a value of a system matrix for a $j^{th}$ image element (voxel) and $i^{th}$ sinogram element of the initial image, and $\tilde{x}_j$ denotes a value of a $j^{th}$ element of the initial image. The system matrix reflects contribution of the initial image to the line of response, i.e., the distribution of probability positron annihilation on the initial image.

In 630, TOF information related to the line of response corresponding to the at least one anomaly detection unit may be estimated according to the third sinogram.

Since the initial image has the TOF information, the third sinogram generated by performing the forward projection on the initial image also may have the TOF information. For example, the third sinogram may reflect a distribution of Time of Flight differences (also referred to as "second TOF value") of the second coincidence events on the line of response corresponding to the at least one anomaly detection unit (e.g., what is a count of second coincidence events corresponding to different second TOF values or what is a proportion of the count to a total count of second coincidence events). In some embodiments, the processing device 140 may obtain the distribution of the second TOF values of the second coincidence events based on the third sinogram. The processing device 140 may use the distribution of the second TOF values of the second coincidence events as the TOF information related to the line of response corresponding to the at least one anomaly detection unit. More descriptions regarding the estimating the TOF information may be found elsewhere in the present disclosure (e.g., FIG. 7 and the related descriptions thereof).

FIG. 7 is a flowchart illustrating an exemplary process for recovering Time of Flight values (i.e., TOF value) of coincidence events on a line of response corresponding to a bad channel (i.e., at least one anomaly detection unit) according to some embodiments of the present disclosure. In some embodiments, the process 700 may be performed by the processing device 140. For example, the process 700 may be stored in a storage device (such as a self-contained storage unit of the processing device or an external storage device) in the form of a program or an instruction. When the program or instruction is executed, the process 700 may be implemented. In some embodiments, the process 700 may include the following operations.

In 710, a count of second coincidence events corresponding to each second TOF value may be determined based on a third sinogram.

In some embodiments, the processing device 140 may determine a line of response corresponding to the at least one anomaly detection unit based on the third sinogram. For the line of response corresponding to each anomaly detection unit, the processing device 140 may determine the count of second coincidence events on the line of response and each second TOF value corresponding to the second coincidence event. The processing device 140 may count the count of second coincidence events corresponding to each second TOF value.

In 720, a proportion of a count of second coincidence events corresponding to the each second TOF value to a total count of second coincidence events may be determined as a probability value of each second TOF value.

Merely by way of example, assuming that the total count of second coincidence events is 100, a count of second coincidence events corresponding to the second TOF value of 0 picosecond is 50, a count of second coincidence events corresponding to the second TOF value of 50 picoseconds is 30, and a count of second coincidence events corresponding to the second TOF value of 100 picoseconds is 20, the processing device 140 may determine that the probability value of the second TOF value of 0 picosecond may be 50%, the probability value of the second TOF value of 50 picoseconds may be 30%, and the probability value of the second TOF value of 100 picoseconds may be 20%.

In 730, TOF information related to the line of response corresponding to the at least one anomaly detection unit may be determined according to the probability value of each second TOF value.

In some embodiments, the processing device 140 may determine a distribution of the second TOF values based on the probability value of each second TOF value on the line of response corresponding to the at least the anomaly detection unit. The processing device 140 may determine the distribution of the second TOF values as the TOF information related to the line of response corresponding to the at least one anomaly detection unit, i.e., the TOF information may include the distribution of the second TOF values.

In 740, for each first coincidence event, a second TOF value may be allocated to the first coincidence event as a first TOF value of the first coincidence event according to the TOF information.

In some embodiments, for each first coincidence event, the processing device 140 may perform probability density sampling on the first coincidence event based on the TOF information, and use a second TOF value obtained by sampling as the first TOF value of the first coincidence event, i.e., the first TOF value of each first coincidence event may be determined based on the distribution of the second TOF values. For example, assuming that the distribution of the second TOF values is that a total count of second coincidence events is 100, the count of second coincidence events corresponding to the second TOF value of 0 picosecond is 50, and the count of second coincidence events corresponding to the second TOF value of 50 picoseconds is 30, and the count of second coincidence events corresponding to the second TOF value of 100 picoseconds is 20, the processing device 140 may randomly select a second coincidence event from the distribution. The processing device 140 may allocate the randomly selected second TOF value of the second coincidence event to the first coincidence event as the first TOF value of the first coincidence event. A probability value that the first TOF value of each first coincidence event is allocated with 0 picosecond may be 50%, a probability value that the first TOF value of each first coincidence event is allocated with 50 picoseconds may be 30%, and the probability value that the first TOF value of each first coincidence event is allocated with 100 picoseconds may be 20%, i.e., the distribution of the first TOF values of the first coincidence events may be consistent with the distribution of the second TOF values of the second coincidence events.

FIG. 8 is a flowchart illustrating an exemplary process for PET imaging according to some embodiments of the present disclosure. In some embodiments, the process 800 may be performed by the processing device 140. For example, the process 800 may be stored in a storage device (such as a self-contained storage unit of the processing device or an external storage device) in the form of a program or an instruction. When the program or instruction is executed, the process 800 may be implemented. In some embodiments, the process 800 may include the following operations.

In 810, a PET scanning may be performed on an object.

In some embodiments, the processing device 140 may receive a scanning instruction. The processing device 140 may determine a scanning protocol or a scanning parameter based on the scan instruction. The processing device 140 may control the imaging device 110 to perform the PET scanning on the object based on the scanning protocol or the scanning parameter.

In 820, whether a PET detector has a failure detection unit (i.e., an anomaly detection unit) may be determined. The operation 830 may be performed in response to a determination that there is the anomaly detection unit in the PET detector, or the operation 890 may be performed in response to a determination that there is no anomaly detection unit in the PET detector.

In some embodiments, the processing device 140 may determine a current functional state of each of a plurality of detection units in the PET detector. For example, the processing device 140 may determine the current functional states of the plurality of detection units based on one or more performance parameters. Merely by way of example, the one or more performance parameters of the detection unit may be generated in real time during the scanning of the PET detector. An exemplary performance parameter of the detection unit may include a count rate. The count rate of the detection unit may be determined by dividing a count of single events counted by the detection unit during a certain period of time by the period of time. The count rate of the detection unit obtained in real time may be sent to the processing device 140. The processing device 140 may compare the obtained count rate with a count rate threshold. When the count rate of the detection unit is smaller than the count rate threshold, the processing device 140 may determine that the detection unit is the anomaly detection unit. When the count rate of the detection unit is equal to or exceeds the count rate threshold, the processing device 140 may determine that the detection unit is a normal detection unit. In some embodiments, it may be determined whether the PET detector has the anomaly detection unit through a performance detection device. The processing device 140 may determine whether there is the anomaly detection unit and a specific position (e.g., serial number) of the anomaly detection unit according to a detection result of the performance detection device.

In 830, raw data of the object may be obtained.

In some embodiments, the raw data may include an accurate count of coincidence events on a line of response corresponding to the normal detection unit, and an abnormal count of first coincidence events on a line of response corresponding to the anomaly detection unit. More descriptions regarding the raw data may be found elsewhere in the present disclosure (e.g., the operation 410 of the process 400 shown in FIG. 4 and the related descriptions thereof).

In 841, an initial image of the object may be generated based on the raw data.

In some embodiments, the processing device 140 may generate the initial image of the object by reconstructing the raw data through TOF reconstruction. The initial image may be a relatively rough image that shows a contour of the object. More descriptions regarding the generating the initial image may be found elsewhere in the present disclosure (e.g., the operation 610 of the process 600 shown in FIG. 6 and the related descriptions thereof).

In 842, a third sinogram may be generated by performing a forward projection on the initial image.

In some embodiments, the third sinogram may be a sinogram with TOF information. For example, the third sinogram may include a distribution of TOF values of second coincidence events on the line of response corresponding to the anomaly detection unit. More descriptions regarding the generating the third sinogram may be found elsewhere in the present disclosure (e.g., the operation 620 of the process 600 shown in FIG. 6 and the related descriptions thereof).

In 851, a first sinogram may be generated based on the raw data.

In some embodiments, the count of first coincidence events on the line of response corresponding to the anomaly detection unit in the first sinogram may be abnormal. In some embodiments, the processing device 140 may generate an initial sinogram based on the raw data. The processing device 140 may generate a second sinogram by performing compression based on the initial sinogram. More descriptions regarding the generating the first sinogram may be found elsewhere in the present disclosure (e.g., the operation 510 of the process 500 shown in FIG. 5 and the related descriptions thereof.

In 852, the second sinogram may be generated based on the first sinogram.

In some embodiments, the processing device 140 may generate the second sinogram by repairing the first sinogram by means of interpolation or deep learning. The second sinogram may include an estimated count of first coincidence events on the line of response corresponding to the anomaly detection unit. More descriptions regarding the generating the second sinogram may be found elsewhere in the present disclosure (e.g., the operation 520 of the process 500 shown in FIG. 5 and the related descriptions thereof).

In 860, a first TOF value of each first coincidence event in the second sinogram may be determined through probability density sampling according to the TOF information in the third sinogram.

In some embodiments, the processing device 140 may determine a count of and the second TOF values of the second coincidence events on the line of response corresponding to the anomaly detection unit based on the third sinogram. The processing device 140 may count the count of second coincidence events corresponding to each second TOF value to determine a distribution of the second TOF values of the second coincidence events on the line of response corresponding to the anomaly detection unit. The processing device 140 may allocate a second TOF value to each first coincidence event in the second sinogram through the probability density sampling based on the distribution of the second TOF values as the first TOF value of the first coincidence event. More descriptions regarding the determining the first TOF value of each first coincidence event in the second sinogram may be found elsewhere in the present disclosure (e.g., the process 700 shown in FIG. 7 and the related descriptions thereof).

In 870, a fourth sinogram may be generated.

In some embodiments, the processing device 140 may generate the fourth sinogram based on the raw data and the first TOF value of the first coincidence event. The fourth sinogram may be a TOF sinogram, including the estimated count of and the estimated first TOF values the first coincidence events on the line of response corresponding to the anomaly detection unit. More descriptions regarding the generating the fourth sinogram may be found elsewhere in the present disclosure (e.g., the operation 450 of the process 400 shown in FIG. 4 and the related descriptions thereof).

In 881, a fifth sinogram may be generated based on the fourth sinogram.

In some embodiments, the processing device 140 may generate the fifth sinogram by rearranging the fourth sinogram according to a PET reconstruction requirement. A pixel of the fifth sinogram may be accurate to a first level (e.g., a millimeter level). A pixel of the fourth sinogram may be accurate to a second level (e.g., a centimeter level). More descriptions regarding the fifth sinogram may be found elsewhere in the present disclosure (e.g., the operation 450 of the process 400 shown in FIG. 4 and the related descriptions thereof).

In 882, list data may be generated based on the fourth sinogram.

In some embodiments, the processing device 140 may generate the list data by rearranging the fourth sinogram.

In 890, a PET image of the object may be generated.

In some embodiments, when the PET detector does not have the anomaly detection unit, the processing device 140 may generate the PET image of the object directly based on the raw data of the object. In some embodiments, when the PET detector has the anomaly detection unit, the processing device may generate the fifth sinogram in the operation 881 or the list data in the operation 882 based on repairing the raw data of the object. The processing device may generate the PET image of the object by performing image reconstruction based on the fifth sinogram or list data. More descriptions regarding the image reconstruction may be found elsewhere in the present disclosure (e.g., the operation 450 of the process 400 shown in FIG. 4 and the related descriptions thereof).

FIG. 10 are exemplary initial sinograms and repaired sinograms according to some embodiments of the present disclosure. As in FIG. 10, a sinogram 1001-1, a sinogram 1003-1, a sinogram 1005-1, and a the sinogram 1007-1 may be the initial sinograms obtained by rearranging the raw data with abnormal counts collected by the PET detector. By performing the sinogram repair manner described in the present disclosure (e.g., operations 410-450 and/or the relevant descriptions of operations 810-890) on the initial sinograms, a repaired sinogram 1001-2, sinogram 1003, sinogram 1005-2, and sinogram 1007-2 may be obtained. The sinogram 1001-2 may be a repaired sinogram corresponding to the initial sinogram 1001-1, the sinogram 1003-2 may be a repaired sinogram corresponding to the initial sinogram 1003-1, and the sinogram 1005-2 may be a repaired sinogram corresponding to the initial sinogram 1005-1, and the sinogram 1007-2 may be a repaired sinogram corresponding to the initial sinogram 1007-1. By comparison, artifacts in the repaired sinogram may be lower than those in the corresponding initial sinogram.

It should be noted that the above descriptions about each process are merely provided for the purpose of illustration, and not intended to limit the scope of application of the present disclosure. For those skilled in the art, various modifications and changes may be made to each process under the guidance of the present disclosure. However, such modifications and changes are still within the scope of the present disclosure. For example, a storage operation may be added into each process, etc.

FIG. 11 is a block diagram illustrating an exemplary medical imaging system according to some embodiments of the present disclosure. In some embodiments, the medical imaging system 1100 may include a radiation event obtaining module 1110, a first response information determination 1120, a second response information determination module 1130, and an image generation module 1140.

The radiation event obtaining module 1110 may be configured to obtain radiation events.

The first response information determination module 1120 may be configured to determine first response information based on the radiation events. The first response information may include first time information of the radiation events.

The second response information determination module 1130 may be configured to determine second response information based on the radiation events. The second response information may include response information corresponding to an anomaly detection unit and lack time information.

The image generation 1140 may be configured to generate an image (also referred to as a first image) based on the first response information and the second response information.

FIG. 12 is a block diagram illustrating an exemplary imaging system (e.g., a PET imaging system) according to some embodiments of the present disclosure. In some embodiments, the imaging system 1200 may include an obtaining module 1210, a count estimation module 1220, a TOF information estimation module 1230, a TOF value estimation module 1240, and a reconstruction module 1250. In some embodiments, each module in the imaging system 1200 may be implemented by the processor 140.

The obtaining module 1210 may be configured to obtain information/data related to imaging. In some embodiments, the obtaining module 1210 may be configured to obtain raw data of an object. More descriptions regarding the raw data may be found elsewhere in the present disclosure (e.g., the operation 410 of the process 400 shown in FIG. 4 and the related descriptions thereof). In some embodiments, the obtaining module 1210 may obtain a scanning instruction to scan the object.

The count estimation module 1220 may be configured to estimate a count of first coincidence events on a line of response corresponding to at least one anomaly detection unit in a PET detector. In some embodiments, the count estimation module may estimate the count of first coincidence events on the line of response corresponding to the at least one anomaly detection unit based on the raw data by means of interpolation or deep learning. More descriptions regarding the count estimation may be found elsewhere in the present disclosure (e.g., the operation 420 of the process 400 shown in FIG. 4 and the related description thereof).

The TOF information estimation module 1230 may be configured to estimate the TOF information related to the line of response corresponding to the at least one anomaly detection unit. In some embodiments, the TOF information estimation module 1230 may estimate the TOF information related to the line of response corresponding to the at least one abnormal unit through TOF reconstruction and forward projection according to the raw data. More descriptions regarding the TOF information estimation may be found elsewhere in the present disclosure (e.g., the operation 430 of the process 400 shown in FIG. 4 and the related description thereof).

The TOF value estimation module 1240 may be configured to estimate first TOF values of the first coincidence events on the line of response corresponding to the at least one anomaly detection unit. In some embodiments, the TOF value estimation module 1240 may estimate the first TOF values of the first coincidence events on the line of response corresponding to the at least one anomaly detection unit through probability density sampling based on the TOF information. More descriptions regarding the TOF value estimation may be found elsewhere in the present disclosure (e.g., the operation 440 of the process 400 shown in FIG. 4 and the related description thereof).

The reconstruction module 1250 may be configured for image reconstruction. In some embodiments, the reconstruction module 1250 may generate a PET image of the object according to the raw data and the first TOF values of the first coincidence events. More descriptions regarding the image reconstruction may be found elsewhere in the present disclosure (e.g., the operation 450 of the process 400 shown in FIG. 4 and the related description thereof).

It should be understood that the system and modules thereof shown in FIG. 1 may be implemented in various ways. For example, in some embodiments, at least one of the obtaining module 1210, the count estimation module 1220, the TOF information estimation module 1230, the TOF value estimation module 1240, and the reconstruction module 1250 may be implemented entirely by hardware, software, or by a combination of software and hardware. As another example, the obtaining module 1210, the count estimation module 1220, the TOF information estimation module 1230, the TOF value estimation module 1240, and/or the reconstruction module 1250 may share a processor and a non-transitory storage medium. Alternatively, each of the obtaining module 1210, the count estimation module 1220, the TOF information estimation module 1230, the TOF value estimation module 1240, and/or the reconstruction module 1250 may have an individual processor and an individual non-transitory storage medium. The non-transitory storage medium may store a computer program. When the processor executes the computer program, a corresponding function may be implemented.

It should be noted that the above description of the medical imaging system and modules thereof is merely for convenience of illustration, and not intended to limit the present disclosure within the scope of the illustrated embodiments. It is understood that for those skilled in the art, after understanding the principle of the system, it may be possible to arbitrarily combine various modules to form a sub-system to connect with other modules without departing from the principle. In some embodiments, the obtaining module 1210, the count estimation module 1220, the TOF information estimation module 1230, the TOF value estimation module 1240, and the reconstruction module 1250 disclosed in FIG. 1 may be different modules in one system or one module implementing the functions of two or more modules. For example, each module may share one storage module, or each module may have its own storage module. Such deformations are within the protection scope of the present disclosure.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various compo- nents described above may be embodied in a hardware device, it may also be implemented as a software only solution, e.g., an installation on an existing server or mobile device.

Similarly, it should be appreciated that in the foregoing description of embodiments of the present disclosure, vari- ous features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodi- ments of the present disclosure are to be understood as being modified in some instances by the term "about," "approxi- mate," or "substantially." For example, "about," "approxi- mate," or "substantially" may indicate ±20% variation of the value it describes, unless otherwise stated. Accordingly, in some embodiments, the numerical parameters set forth in the written description and attached claims are approxima- tions that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodi- ments of the present disclosure are not limited to that precisely as shown and described.

34

What is claimed is:

1. A method for positron emission tomography (PET) imaging, comprising:
   obtaining radiation events;
   determining first response information based on the radia- tion events, the first response information including first time information of the radiation events;
   determining second response information based on the radiation events, the second response information including response information corresponding to a defective detector and lacking time information; and
   generating an image based on the first response informa- tion and the second response information.

2. The method of claim 1, wherein the generating the image based on the first response information and the second response information includes:
   for the response information corresponding to the defec- tive detector, obtaining updated second response infor- mation by allocating second time information to the response information based on the first time informa- tion; and
   generating the image based on the updated second response information.

3. The method of claim 2, wherein for the response information corresponding to the defective detector, the obtaining the updated second response information by allo- cating the second time information to the response informa- tion based on the first time information includes:
   determining a time distribution of a reference line of response based on the first time information of the first response information, wherein the reference line of response has a position correspondence relationship with a line of response corresponding to the defective detector;
   determining a total count of radiation events on the line of response corresponding to the defective detector; and
   allocating the second time information to the second response information based on the time distribution and the total count of radiation events on the line of response corresponding to the defective detector.

4. The method of claim 3, wherein the time distribution includes a distribution of Time of Flight differences in different periods of time.

5. The method of claim 4, wherein the allocating the second time information to the second response information based on the time distribution and the total count of radiation events on the line of response corresponding to the defective detector includes:
   for each radiation event on the line of response corre- sponding to the defective detector, determining a Time of Flight based on a period of time of the different periods of time.

6. The method of claim 5, further comprising:
   converting the time distribution into a probability distri- bution, wherein the probability distribution is config- ured to reflect a probability of allocating a certain period of time to each radiation event on the line of response corresponding to the defective detector.

7. The method of claim 1, wherein an accuracy level of the first response information and an accuracy level of the second response information are adjustable.

8. The method of claim 1, wherein the determining the first response information based on the radiation events includes:
   generating a second image based on the radiation events; and determining the first response information based on the second image.

9. The method of claim 8, wherein the radiation events include first radiation events, each of the first radiation events has a corresponding Time of Flight, the generating the second image based on the radiation events includes:

for each first radiation event of the first radiation events, determining an ideal annihilation position according to a Time of Flight corresponding to the first radiation event;

obtaining a broadened annihilation position by broadening the ideal annihilation position; and generating the second image based on the broadened annihilated positions.

10. The method of claim 8, wherein the determining the first response information based on the second image includes:

obtaining a forward projection result by performing a forward projection on the second image; and determining the first response information based on the forward projection result.

11. The method of claim 1, wherein the determining the second response information based on the radiation events includes:

obtaining initial response information based on the radiation events; and determining the second response information by performing a data repair process on the initial response information.

12. A system for positron emission tomography (PET) imaging, comprising:

at least one storage device storing a set of instructions; and at least one processor in communicate with the storage device, wherein when executing the set of instructions, the at least one processor is configured to cause the system to perform operations including:

obtaining radiation events;

determining first response information based on the radiation events, the first response information including first time information of the radiation events;

determining second response information based on the radiation events, the second response information including response information corresponding to a defective detector and lacking time information; and generating an image based on the first response information and the second response information.

13. The system of claim 12, wherein the at least one processor is further configured to cause the system to perform operations including:

for the response information corresponding to the defective detector, obtaining updated second response information by allocating second time information to the response information based on the first time information; and reconstructing the image based on the updated second response information.

14. The system of claim 13, wherein the at least one processor is further configured to cause the system to perform operations including:

determining a time distribution of a reference line of response based on the first time information of the first response information, wherein the reference line of response has a position correspondence relationship with a line of response corresponding to the defective detector;

determining a total count of radiation events on the line of response corresponding to the defective detector; and allocating the second time information to the second response information based on the time distribution and the total count of radiation events on the line of response corresponding to the defective detector.

15. The system of claim 14, wherein the time distribution includes a distribution of Time of Flight differences in different periods of time.

16. The system of claim 15, wherein the at least one processor is further configured to cause the system to perform operations including:

for each radiation event on the line of response corresponding to the defective detector, determining a Time of Flight based on a period of time of the different periods of time.

17. The system of claim 16, wherein the at least one processor is further configured to cause the system to perform operations including:

converting the time distribution into a probability distribution, wherein the probability distribution is configured to reflect a probability of allocating a certain period of time to each radiation event on the line of response corresponding to the defective detector.

18. A method for positron emission tomography (PET) imaging, comprising:

obtaining raw data of an object, the raw data being obtained by detecting gamma photons by a plurality of detection units of a PET detector and the plurality of detection units including at least one anomaly detection unit;

determining a count of first coincidence events on a line of response corresponding to the at least one anomaly detection unit according to the raw data;

determining Time of Flight information related to the line of response corresponding to the at least one anomaly detection unit according to the raw data;

determining a first Time of Flight value of each of the first coincidence events on the line of response corresponding to the at least one anomaly detection unit according to the Time of Flight information; and generating a PET image of the object according to the raw data and the first Time of Flight value of the each first coincidence event.

19. The method of claim 18, wherein the determining the count of the first coincidence events on the line of response corresponding to the at least one anomaly detection unit according to the raw data includes:

generating a first sinogram according to the raw data, the count of first coincidence events on the line of response corresponding to the at least one anomaly detection unit in the first sinogram being abnormal; and generating a second sinogram according to the first sinogram, the second sinogram including the count of the first coincidence events on the line of response corresponding to the at least one anomaly detection unit.

20. The method of claim 18, wherein the determining Time of Flight information related to the line of response corresponding to the at least one anomaly detection unit according to the raw data includes:

generating an initial image of the object according to the raw data;

generating a third sinogram by performing a forward projection on the initial image; and determining the TOF information related to the line of
response corresponding to the at least one anomaly
detection unit according to the third sinogram.

* * * * *